US 6,875,777 B2
United States Patent
Brown et al.
(10) Patent No.: US 6,875,777 B2
(45) Date of Patent: Apr. 5, 2005

(54) COMPOUNDS

(75) Inventors: William Brown, St. Laurent (CA); Christopher Walpole, St. Laurent (CA)

(73) Assignee: AstraZeneca AB, Sodertalje (SE)

(*) Notice: Subject to any disclaimer, the term of this patent is extended or adjusted under 35 U.S.C. 154(b) by 36 days.

(21) Appl. No.: 10/149,982

(22) PCT Filed: Dec. 15, 2000

(86) PCT No.: PCT/SE00/02560

§ 371 (c)(1),
(2), (4) Date: Jun. 13, 2002

(87) PCT Pub. No.: WO01/46263

PCT Pub. Date: Jun. 28, 2001

(65) Prior Publication Data

US 2003/0036552 A1 Feb. 20, 2003

(30) Foreign Application Priority Data

Dec. 20, 1999 (SE) ................................. 9904675

(51) Int. Cl.$^7$ ...................... A61K 31/445; C07D 213/72
(52) U.S. Cl. ........................ 514/329; 546/223; 546/224
(58) Field of Search ......................... 514/329; 546/223, 546/224

(56) References Cited

U.S. PATENT DOCUMENTS

| | | | | |
|---|---|---|---|---|
| 4,091,096 | A | 5/1978 | Beck et al. | 514/157 |
| 4,126,689 | A | 11/1978 | Sanczuk et al. | 514/329 |
| 4,460,586 | A | 7/1984 | Berthold | 514/254.09 |
| 4,680,296 | A | 7/1987 | Manoury et al. | 514/259 |
| 5,118,693 | A | 6/1992 | Toth et al. | 514/327 |
| 5,132,303 | A | 7/1992 | Toth et al. | 514/278 |
| 5,132,309 | A | 7/1992 | Toth et al. | 514/278 |
| 5,854,245 | A | 12/1998 | Duggan et al. | 514/250 |
| 6,153,626 | A | 11/2000 | Pelcman et al. | 514/329 |
| 6,399,635 | B1 | 6/2002 | Pelcman et al. | 514/329 |
| 6,436,959 | B1 * | 8/2002 | Carson et al. | 514/326 |

FOREIGN PATENT DOCUMENTS

| | | | | |
|---|---|---|---|---|
| DE | 28 22 465 | 11/1978 | ......... | C07D/471/04 |
| HU | 206 677 | 8/1989 | ......... | C07D/211/22 |
| WO | WO 98/28270 | 7/1998 | ......... | C07D/211/56 |
| WO | WO 99/33806 | 7/1999 | ......... | C07D/211/58 |
| WO | WO 99/45925 | 9/1999 | ......... | A61K/31/435 |

OTHER PUBLICATIONS

Bilsky, et al., SNC 80, A Selective, Nonpeptidic and Systemically Active Opioid *Delta* Agonist, *J. Pharmacol. Experi. Ther.* 273:359–366 (1995).

Enein, et al., Abstract #159379n, "Synthesis of Some 4–Substituted Amino–1–Methyl Piperidines Structurally Related to Antihistaminics," *Chem. Abstr.* 78:396 (1973).

Laskowska, Abstract #105299e, "1–Methyl–r–[N–phenyl–N–(2–thienyl)amino]piperidine," *Chem. Abstr.* 81:510 (1974).

Podlogar, et al., "Synthesis and Evaluation of 4–(N,N–Diarylamino)piperidines with High Selectivity to the o–Opioid Receptor: A Combined 3D–QSAR and Ligand Docking Study," *Drugs Design and Discovery*, 34–50 (2000).

Sarges, et al., "Neuroleptic Activity of Chiral *trans*–Hexahydroγ–Carbvolines," *J. Med. Chem.* 29:8–19 (1986).

Takemori, et al., "Selective Natrexone–Derived Opioid Receptor Antagonists," *Pharmacol. Toxicol.* 32:239–269 (1992).

Abstract for AKI above.

Abstract of AH 1 above.

English language abstract of AH 1 above.

Adachi, et al., "Aminohaloborane in Organic Synthesis. IX. Exclusive Ortho Acylation Reacfdtion of N–Monoaminoalkylanilines," XP002277753, Database Chemabs Online, Accession No. 1987:49715, *Chemical & Pharmaceutical Bulletin* 33(5):1826–1835 (1985).

(Continued)

*Primary Examiner*—Celia Chang
(74) *Attorney, Agent, or Firm*—Michael A. Sanzo; Fitch, Even, Tabin & Flannery

(57) ABSTRACT

The present application is directed to compounds having the structure of Formula I:

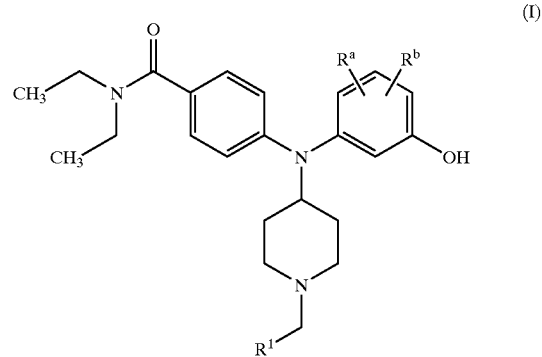

where $R^1$ is phenyl, pyridinyl, thiophenyl, furanyl, imidazolyl or trazolyl, each optionally substituted by a straight or branched $C_1$–$C_6$ alkyl, $NO_2$, $CF_3$, $C_1$–$C_6$ alkoxy, chloro, fluoro, bromo, or iodo;

where $R^a$ and $R^b$ are independently selected from hydrogen, a straight or branched $C_1$–$C_6$ alkyl, $NO_2$, $C_1$–$C_6$ alkoxy, chloro, fluoro, bromo, or iodo; and where X is O or $CH_3$.

The compounds may be incorporated into pharmaceutical compositions and administered to patients as a treatment for pain, gastrointestinal disorders, spinal injury, or disorders of the sympathetic nervous system.

10 Claims, No Drawings

OTHER PUBLICATIONS

Burkartsmaier, et al., "Potential Analgesics, IX: Synthesis and Pharmacological Test of Substituted N–(Piperidin–4–yl)Anthranilic Acid Derivatives," XP002277757, Database Chemabs Online, Accession No. 1979:54780, *Archiv. der Pharmazie 311(10)*:843–848 (1978).

Deruiter, et al., "Investigation of the Synthesis and Analgesic Activity of 1–Substituted 4–(Propananilido) Perhydroazepines," XP002277751, Database Chemabs Online, Accession No. 1992:612296, *J. Heterocyclic Chem. 29(4)*:779–786 (1996).

Ferrand, et al., "Synthesis of new 1,2,3–triazin–4–Ones as Potential Antidepressants," XP002277752, Database Chemabs Online, Accession No. 1988:150431, *Eur. J. Medicinal Chem. 22(4)*:337–345 (1987).

Obase, et al., "New Antihypertensive Agents. III. Synthesis and Antihypertensive Activity of Some Arylalkyl Piperidines Carrying a Hetcrocycle at the 4–Position," XP002277758, Database Chemabs Online, Accession No. 1984:120835, *Chemical & Pharmaceutical Bulletin 31(9)*:3186–3197 (1983).

Sugasawa, et al., "1–Azacycloalkyl–1,4–Benzodiazepin–2–Ones with Antianxiety–Antidepressant Actions," XP002277755, Database Chemabs Online, Accession No. 1985:437458, *J. Medicinal Chem. 28(6)*:699–707 (1985).

Takai, et al., "Synthesis and Pharmacological Evaluations of Piperidine Derivatives with Various Heterocyclic Rings at the 4–Position," XP002277754, Database Chemabs Online, Accession No. 1985:578235, *Chemical & Pharmaceutical Bulletin 33(3)*:1104–1115(1985).

Wang, et al., "Opioid .Delta. Receptor Irreversible Inhibitors. 2. Synthesis of Isothiocyanate Derivatives of Carfentanil and 4–(Methoxymethyl)Fentanyl," XP002277750, Database Chemabs Online, Accession No. 1995:857886, *Chinese Chemical Letters 6(9)*:763–764 (1995).

Zhu, et al., "Studies on Potent Analgesics. I. Synthesis and Analgesic Activity of Fentanyl Derivatives," XP002277756, Database Chemabs Online, Accession No. 1981:550311, *Yaoxue Xuebao 16(3)*:199–210 (1981).

* cited by examiner

COMPOUNDS

CROSS REFERENCE TO RELATED APPLICATIONS

The present application represents U.S. national stage of international application PCT/SE00/02560, which had an international filing date of Dec. 15, 2000, and which was published in English under PCT Article 21(2) on Jun. 28, 2001. The international application claims priority to Swedish application 9904675-7, filed on Dec. 20, 1999.

FIELD OF THE INVENTION

The present invention is directed to novel compounds, to a process for their preparation, their use and pharmaceutical compositions comprising the novel compounds. The novel compounds are useful in therapy, and in particular for the treatment of pain.

BACKGROUND AND PRIOR ART

The δ receptor has been identified as having a role in many bodily functions such as circulatory and pain systems. Ligands for the δ receptor may therefore find potential use as analgesics, and/or as antihypertensive agents. Ligands for the δ receptor have also been shown to possess immunomodulatory activities.

The identification of at least three different populations of opioid receptors ($\mu$, δ and κ) is now well established and all three are apparent in both central and peripheral nervous systems of many species including man. Analgesia has been observed in various animal models when one or more of these receptors has been activated.

With few exceptions, currently available selective opioid δ ligands are peptidic in nature and are unsuitable for administration by systemic routes. One example of a non-peptidic δ-agonist is SNC80 (Bilsky E. J. et al., *Journal of Pharmacology and Experimental Therapeutics*, 273(1), pp. 359–366 (1995)). There is however still a need for selective δ-agonists having not only improved selectivity, but also an improved side-effect profile.

Thus, the problem underlying the present invention was to find new analgesics having improved analgesic effects, but also with an improved side-effect profile over current $\mu$ agonists, as well as having improved systemic efficacy.

Analgesics that have been identified and are existing in the prior art have many disadvantages in that they suffer from poor pharmacokinetics and are not analgesic when administered by systemic routes. Also, it has been documented that preferred δ agonist compounds, described within the prior art, show significant convulsive effects.

We have now found that certain compounds not specifically disclosed by, but included within the scope of WO 98/28270, exhibit surprisingly improved δ-agonist properties and in vivo potency when administered systemically Relative to compounds disclosed in WO98/28270, the compounds of the present invention exhibit significant and unexpected increased levels of delta receptor agonism and metabolic stability.

OUTLINE OF THE INVENTION

The novel compounds according to the present invention are defined by the formula I

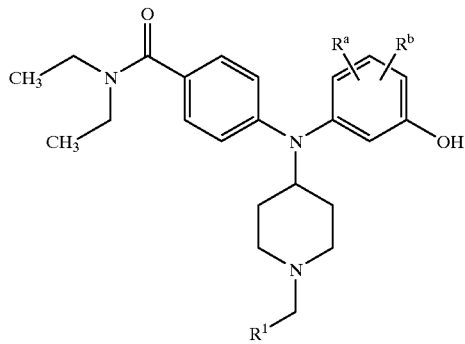

wherein
R$^1$ is selected from any one of
(i) phenyl;

(ii)
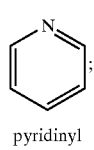
pyridinyl (iii)
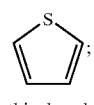
thiophenyl (iv)
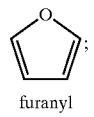
furanyl (v)
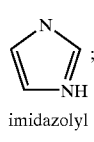
imidazolyl (vi)
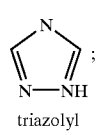
triazolyl where each R$^1$ phenyl ring and R$^1$ heteroaromatic ring may optionally and independently be further substituted by 1, 2 or 3 substituents selected from straight and branched $C_1$–$C_6$ alkyl, $NO_2$, $CF_3$, $C_1$–$C_6$ alkoxy, chloro, fluoro, bromo, and iodo. The substitutions on the phenyl ring and on the heteroaromatic ring may take place in any position on said ring systems;

$R^a$ and $R^b$ is each and independently selected from any one of hydrogen, a straight and branched $C_1$–$C_6$ alkyl, $NO_2$, $CF_3$, $C_1$–$C_6$ alkoxy, chloro, fluoro, bromo, and iodo. The $R^a$ and $R^b$ substituents may be positioned in any one of ortho-, meta- and para-position of the phenol ring. Preferably, $R^a$ and $R^b$ are both hydrogen.

Within the scope of the invention are also pharmaceutically acceptable salts of the compounds of the formula I.

When the phenyl ring and the heteroaromatic ring(s) are substituted, the preferred substituents are selected from anyone of $CF_3$, methyl, iodo, bromo, fluoro and chloro.

The novel compounds of the present invention are useful in therapy, especially for the treatment of various pain conditions such as chronic pain, neuropathic pain, acute pain, cancer pain, pain caused by rheumatoid arthritis, migraine, visceral pain etc. This list should however not be interpreted as exhaustive.

Compounds of the invention are useful as immunomodulators, especially for autoimmune diseases, such as arthritis, for skin grafts, organ transplants and similar surgical needs, for is collagen diseases, various allergies, for use as anti-tumour agents and anti viral agents.

Compounds of the invention are useful in disease states where degeneration or dysfunction of opioid receptors is present or implicated in that paradigm. This may involve the use of isotopically labelled versions of the compounds of the invention in diagnostic techniques and imaging applications such as positron emission tomography (PET).

Compounds of the invention are useful for the treatment of diarrhoea, depression, anxiety, urinary incontinence, various mental illnesses, cough, lung oedema, various gastrointestinal disorders, spinal injury and drug addiction, including the treatment of alcohol, nicotine, opioid and other drug abuse and for disorders of the sympathetic nervous system for example hypertension.

Compounds of the invention are useful as an analgesic agent for use during general anaesthesia and monitored anaesthesia care. Combinations of agents with different properties are often used to achieve a balance of effects needed to maintain the anaesthetic state (e.g. amnesia, analgesia, muscle relaxation and sedation). Included in this combination are inhaled anaesthetics, hypnotica, anxiolytics, neuromuscular blockers and opioids.

Also within the scope of the invention is the use of any of the compounds according to the formula I above, for the manufacture of a medicament for the treatment of any of the conditions discussed above.

A further aspect of the invention is a method for the treatment of a subject suffering from any of the conditions discussed above, whereby an effective amount of a compound according to the formula I above, is administered to a patient in need of such treatment.

Also within the scope of the present invention are intermediate compounds of formula II which are useful for synthesis of compounds of formula I above

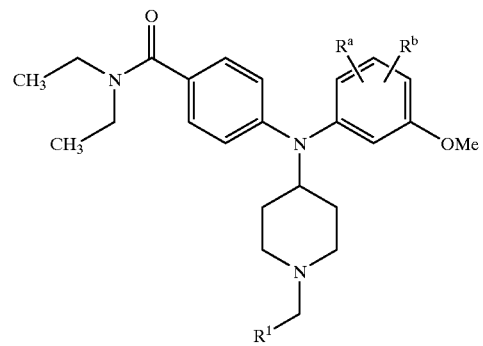

wherein $R^1$ is selected from any one of (i) phenyl;

(ii) pyridinyl 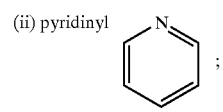;

(iii) thiophenyl 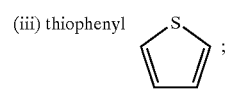;

(iv) furanyl 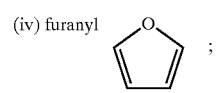;

(v) imidazolyl 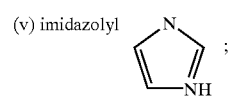;

(vi) triazolyl 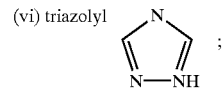;

where each $R^1$ phenyl ring and $R^1$ heteroaromatic ring may optionally and independently be further substituted by 1, 2 or 3 substituents selected from straight and branched $C_1$–$C_6$ allyl, $NO_2$, $CF_3$, $C_1$–$C_6$ alkoxy, chloro, fluoro, bromo, and iodo. The substitutions on the phenyl ring and on the heteroaromatic ring may take place in any position on said ring systems; $R^a$ and $R^b$ is each and independently selected from any one of hydrogen, a straight and branched $C_1$–$C_6$ alkyl, $NO_2$, $CF_3$, $C_1$–$C_6$ alkoxy, chloro, fluoro, bromo, and iodo;

Methods of Preparation

I. The compounds according to the present invention may be prepared by following the procedure described in Scheme I below. These known procedures are described in *C. G. Frost and P. Mendonca; Perkin* 1 (1998), 2615; *and in J. F. W. McOmie, M. L Watts, D. E. West, Tetrahedron*, 1969, 24, 2289; which are hereby incorporated by reference.

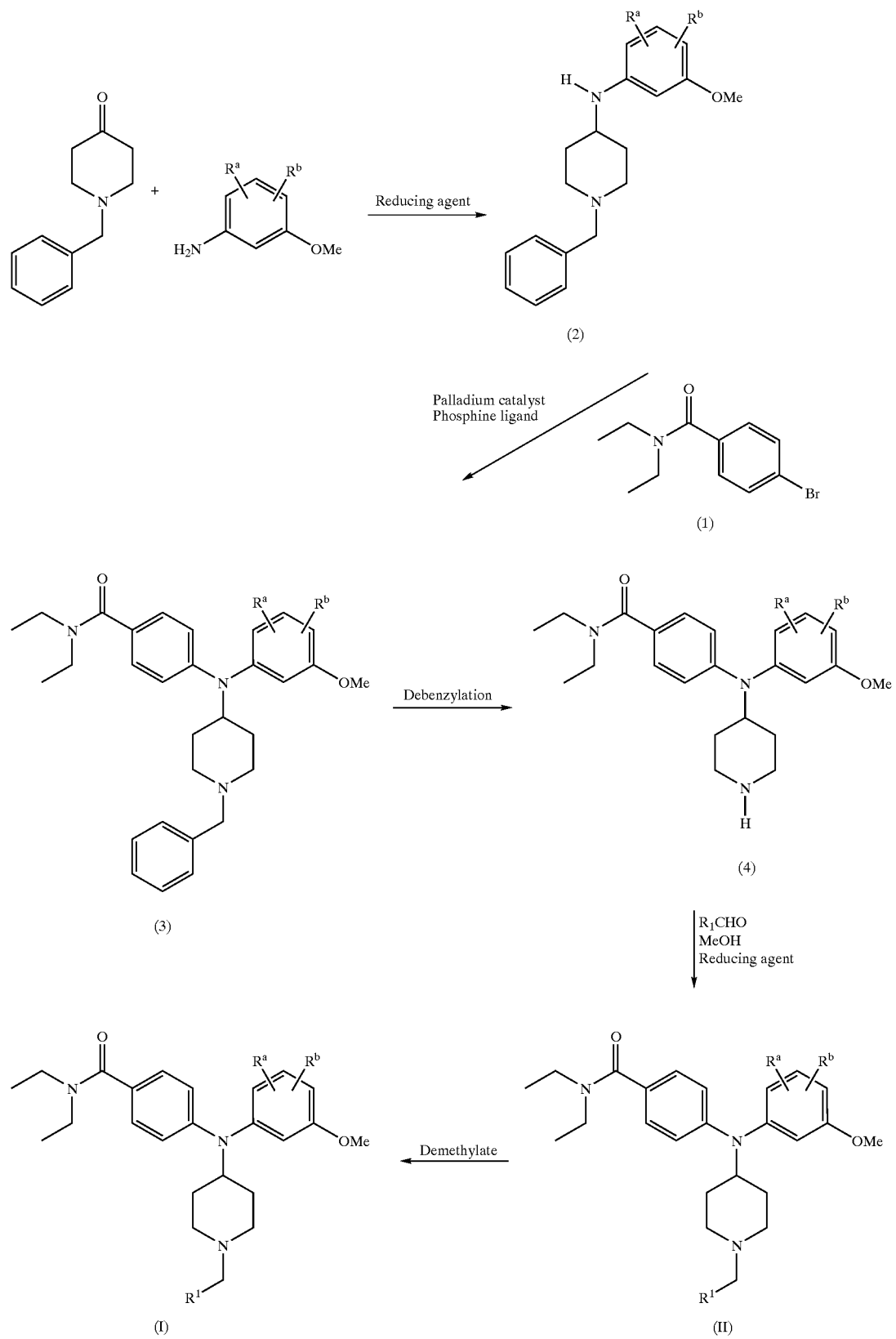
Scheme 1

In Scheme I above, $R^1$, $R^a$ and $R^b$ are as defined for compounds of formula I above.

II. Alternatively the synthesis may proceed as in Scheme 2, below, via one-pot double arylation (described in C. G. Frost and P. Mendonca; *Perkin* 1 (1998), 2615) of commercially available 4-amino-1-benzylpiperidine to yield intermediate 3 from Scheme 1. For $R^1$=phenyl, the final product may then be prepared by selective ether cleavage (J. F. W. McOmie, M. L. Watts, D. E. West, *Tetrahedron*, 1969, 24, 2289) as in Scheme 2, below.

Scheme 2

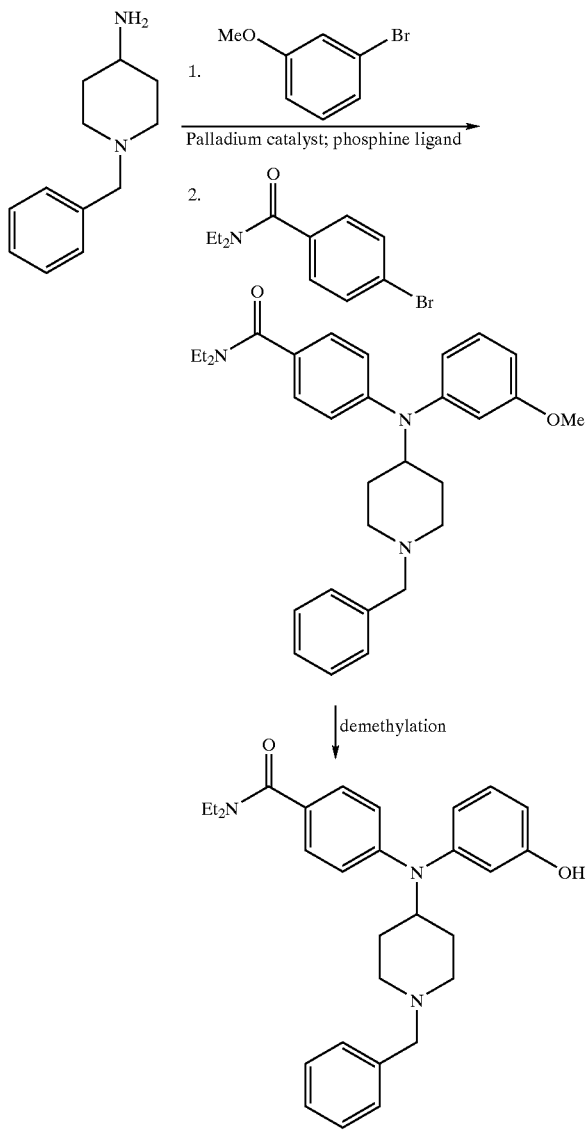

EXAMPLES

The invention will now be described in more detail by the following Examples, which are not to be construed as limiting the invention.

I.

(i) Preparation of 4-bromo-N,N-diethyl benzamide (compound 1).

To an ice cooled solution of 4-bromobenzyl chloride (19.5 g, 86.8 mmol) in 150 ml of $CH_2Cl_2$ was added dropwise (13.5 ml, 130 mmol) of diethylamine. The reaction is stirred overnight then concentrated. The mixture is taken into ether and 1 HCl and the aqueous layer separated. The organic layer was extracted a further two times with ether then washed with brine and dried over $Na_2SO_4$. The resulting oil was taken into ethyl acetate and allowed to crystallize. 2 more crystallizations of the mother liquor yielded 18.6 g, 83.6%.

(ii) Preparation of N-(3-methoxyphenyl)-1-(phenylmethyl)-4-piperidinamine (compound 2).

To 1-benzyl piperidone (10 ml, 0.56 mmol) and 3-methoxyaniline (7.5 ml, 67.2 mmol) is added Ti(i-OPr)$_4$. (33.3, 112.06 mmol) The reaction is stirred to completion as determined by GC. EtOH (200 ml) is then added, followed by NABH$_4$ (3.18 g, 84 mmol). The reaction is stirred at RT. Progress of the reaction was monitored by GC. On completion, NH$_4$OH is added to the white mixture and stirring is continued for a further 30 mins. This is then diluted with $CH_2Cl_2$, followed by the addition of Celite. The resulting paste is filtered and the filtrate extracted several times with $CH_2Cl_2$. The combined organic phases are concentrated and the product purified by flash chromatography (1:1, hexanes:acetone) Yielded 13.6 g, 82%. Purification may also be achieved by Kugelrohr distillation under high vacuum at $2\times10^{-3}$ m bar at approx. 225° C. 25.6 g of benzylpiperidone yielded 28.4 g, 71.6% of.

(iii) Preparation of N,N-diethyl-4-[(3-methoxyphenyl)[1-(phenylmethyl)-4-piperidinyl]amino]-3 benzamide (compound 3).

To a 250 ml RB flask, in a dry box under $N_2$ atmosphere, was added 10 g (0.34 mmol, 1 eq) of 2, 13 g (50.7 mmol, 1.5 eq) of 1, Pd$_2$(dba)$_3$ (783 mg, 0.85 mmol), BINAP (784 mg, 1.26 mmol), and Nat-OBu, (6,53 g, 68 mmol, 2 eq). To this was canulated toluene to three-quarters of the volume of the flask. The mixture was then heated at 110° C. for approx. 6 hrs to the disappearance of 2, as determined by HPLC. The reaction was allowed to cool. Ether is added then the suspension is filtered through Celite and concentrated. This oil was taken into ether and allowed to stand for 15 minutes and then filtered again through Celite. The filtrate was extracted 5 times with 2 N HCl. The aqueous phase was then made basic with 4 N NaOH and extracted with ether. The combined ether layers were dried over $Na_2SO_4$, filtered and concentrated. The resulting oil was taken into ethyl acetate/hexane and let stand over weekend. 8 g of solid (50%) was recovered by filtration, and washed with ethyl acetate/hexanes, 8/2. The remaining product, from the concentrated mother liquor, was not isolated.

(iv) Preparation of N,N-diethyl-4-[(3-methoxyphenyl)-4-piperidinylamino]-benzamide (compound 4).

To a solution of 3 (2.5 g, 5.3 mmol) in 1,2-dichloroethane at 0° C. was added α-chloroethyl chloroformate (0.93 ml, 8.6 mmol). The reaction was then refluxed for 3 hours and stirred over night at R/T. The solvent was removed and the resulting oil was taken into methanol and refluxed for 3 hrs. This was then concentrated taken into $CH_2Cl_2$ and extracted 5 times with 1 N HCl. The combined aqueous layers were made basic with 5 N NaOH and extracted several times with $CH_2Cl_2$. The organic layers were concentrated and the resulting oil purified by flash chromatography on silica gel with $CH_2Cl_2$/2% MeOH increasing the polarity to 20%. Yield: 1.68 g, 83%

II. General Synthesis of Compounds of Formula II.

To a solution of 4 (1.05 mmol, 1 eq) in 10 mL of methanol was added (1.58 mmol, 1.5 eq) of heterocyclic or aromatic aldehyde, followed by NaBH$_3$CN (1.05 mmol, 3 eq). The pH of the reaction was then adjusted to approx. 6 with glacial acetic acid. The reaction is stirred over night. 2 N HCl is added and stirring continued for 1 hour. This was concentrated to remove the methanol made basic with NaOH and extracted with CH$_2$Cl$_2$ followed by drying over Na$_2$SO4 Purification done by silica gel flash chromatography using CH$_2$Cl/MeOH with a gradual gradient. Increasing the polarity from 0.025% to 4% MeOH yields pure product.

III. General Synthesis of Phenol Compounds of Formula I.

To a solution of 5 (1 eq) in CH$_2$Cl$_2$ at −78° C. was added 3 eq of BBr$_3$ (1 M in CH$_2$Cl$_2$). Stirred for approx. 45 minutes then at room temperature for 2 hours. MeOH was added followed by saturated NaHCO$_3$. The phases were separated and the aqueous layer extracted several times with CH$_2$Cl$_2$. The combined organic layers were dried over MgSO$_4$ and concentrated. Purification by flash chromatography over silica gel. CH$_2$Cl$_2$/MeOH, 100/0.25 slowly increasing the quantity of MeOH. A further purification can be achieved in most cases by a crystallisation from ethyl acetate. Purification was also achieved using reverse phase HPLC with a gradient of 0.1% T-FA in H$_2$O/0.1% TFA in CH$_3$CN.

HCl Salt Formation:

To a stirring solution of 1.1 g of free amine in 10 ml of dry CH$_2$Cl$_2$ was added 40 ml of dry ether followed by 20 ml of 1 N HCl in ether. A further 40 ml of dry ether was added and the white suspension stirred for 30 minutes. Under a stream of N$_2$, the solid was collected by filtration and washed with ether. The product is hygroscopic. Before the solid had dried the buchner funnel was placed immediately under house vacuum in a dessicator over night. 1.14 g of white solid was collected. Alternatively the phenol can be dissolved in ethyl acetate, followed by the addition of an excess of 1 N HCl in ether then of ether. Excess ether and HCl are removed under vacuum.

The trifluoroacetic acid salts were recovered following reverse phase preparative HPLC.

Example 1

Preparation of N,N-diethyl-4-[[(3-hydoxyphenyl)[1-(phenylmethyl)-4-piperidinyl]amino]benzamide (Compound 5)

The title compound 5 was prepared by following the synthetic procedure of Scheme I above.

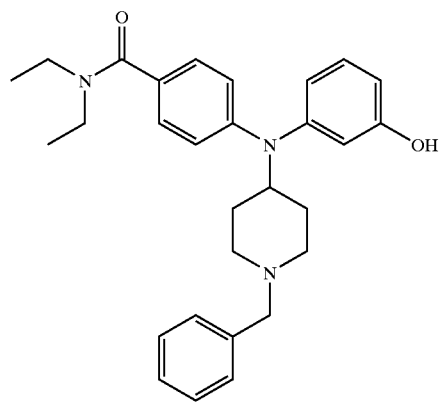

MS: (M+1) calculated: 458.62 (MH+); (M+1) observed: 458.24 (MH+). IR: Film HCl salt: 3047, 2974, 2531, 1600, 1471, 1455, 1283, 1186, 1093, 735, 701 cm$^{-1}$. $^1$H NMR: (400 MHz, CDCl$_3$, TMS, Free amine): 7.39–7.10 (9H, m, Ar), 6.58–6.45 (3H, m, Ar), 6.23–6.22 (1H, m, Ar), 3.83–3.77 (1H, m, CH), 3.52 (3H, s, CH$_3$O), 3.43 (4H, s broad, CH$_2$N), 2.98 (2H, d, CH$_2$), 2.17–2.11 (2H, t, CH$_2$), 1.85 (2H, d, CH$_2$), 1.59–1.51 (2H, m, CH$_2$), 1.20–1.16 (6H, m, CH$_3$).

HPLC:

>95% (215 nm)
>98% (254 nm)
>99% (280 nm)

ANALYSIS:

C$_{29}$H$_{35}$N$_3$O$_2$, ×2.4HCl, ×0.2C$_4$H$_{10}$O, ×0.1CH$_2$Cl$_2$
Found: C 63.20%, H 7.07%, N 7.36%,
Calc.: C 63.18%, H 7.02%, N 7.39%, O 6.19%, Cl 16.22%.

IV. Synthesis of p-halophenol Derivatives p-halophenol derivatives of the formulas (8) and (9) were prepared by following the synthetic Scheme II below.

Scheme II

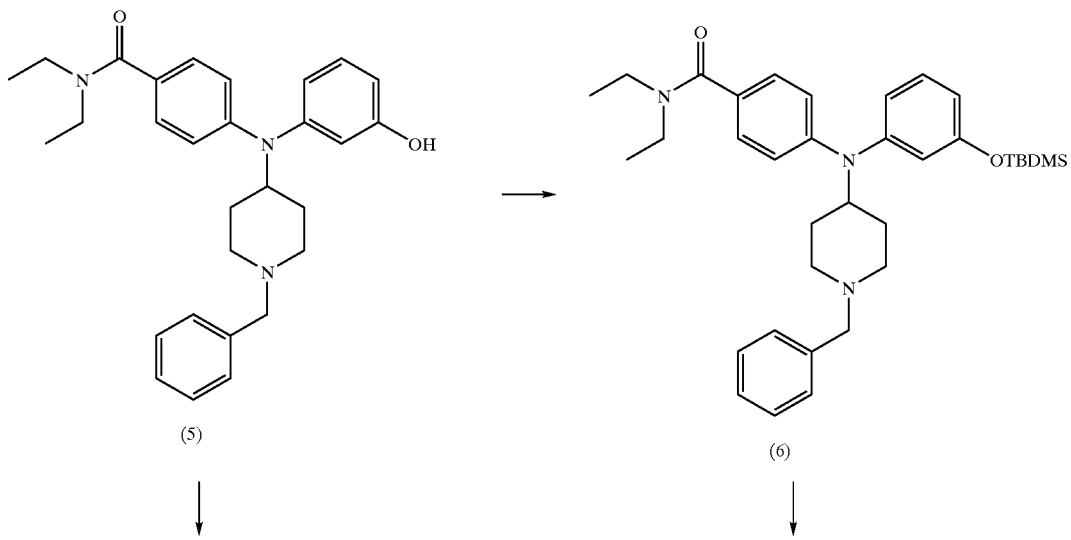

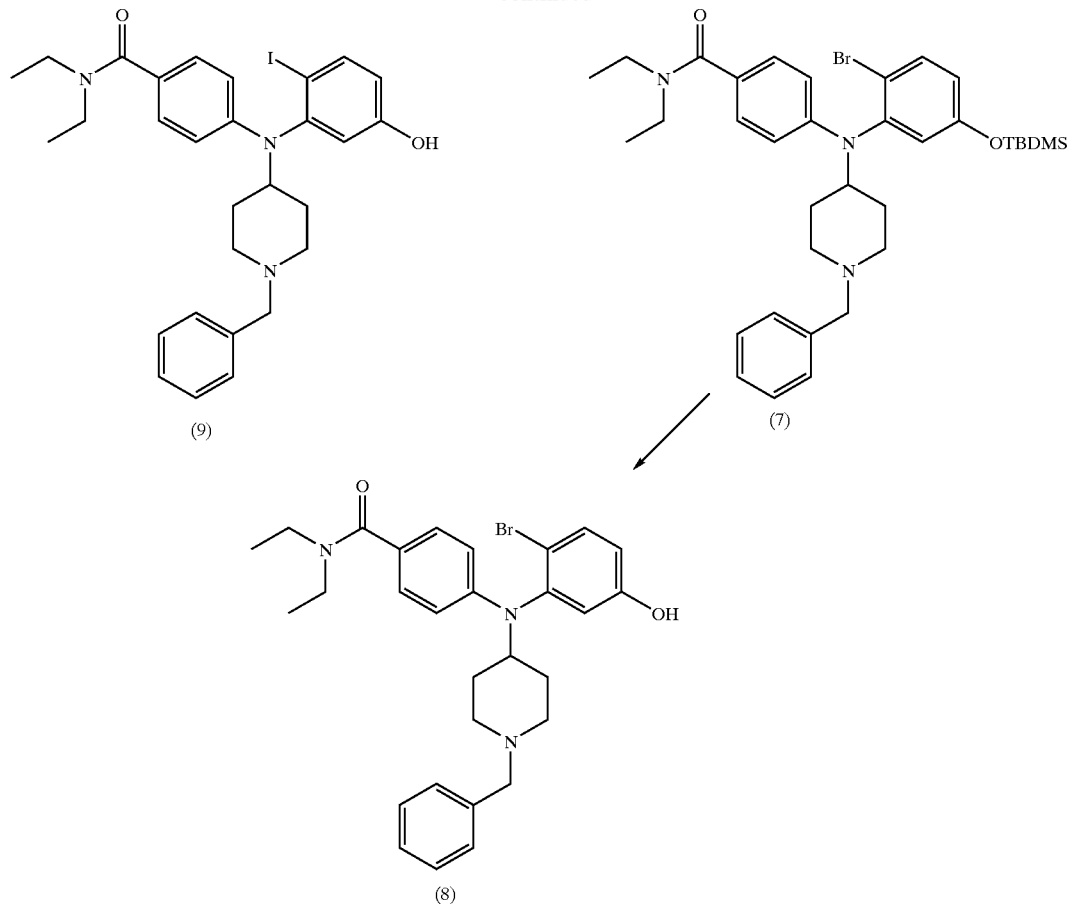

(i) Preparation of N,N-diethyl-4-[[3-[[(1,1-dimethylethyl)dimethylsilyl]oxy]phenyl][1-(phenylmethyl)-4-piperidinyl]amino]-benzamide (compound 6).

(200 mg, 0.4 mmol) of 5, TBDMSCl (302 mg, 2.0 mmol) and imidazole (138 mg, 2.0 mmol) in 15 ml of DMF was heated at 100° C. for 3 hours. The solvent was removed and the resulting oil purified by silica gel flash chromatography using 100% $CH_2Cl_2$ then 1% and 2% MeOH. Yielded 200 mg, 87%.

(ii) Preparation of N,N-diethyl-4-[[2-bromo-5-[[(1,1-dimethylethyl)dimethylsilyl]oxy]phenyl][1-(phenylmethyl)-4-piperidinyl]amino]-benzamide (compound 7).

To a solution of (82.9 mg, 0.145 mmol) of 6 in 6 ml of DMF at 0° C. was added a solution of NBS (27.7 mg, 0.155 mmol) in 2 ml of DMF. The reaction was stirred for 2 hours, concentrated then flashed with 10% acetone/hexanes followed by 20% acetone. Collected 61.25 mg, 65%.

Example 2

Preparation of N,N-diethyl-4-[(2-bromo-5-hydroxyphenyl)[1-(phenylmethyl)-4-piperidinyl]amino]-benzamide (compound 8)

Compound 6 in dioxane was treated with 4 N HCl in dioxane. The reaction is stirred until completion. Purification was accomplished by reverse phase preparative HPLC using $CH_3CN/H_2O$.

Anal. Calcd for C29H34N3O2Br×1.4 CF3CO2H×0.3 H2O: C, 54.44; H, 5.17; N, 5.99;

Found: C, 54.43; H, 5.06; N, 6.05.

M.S (calc'd): 537.15(MH+),

M.S (found): 536.16 (MH+)

HPLC Conditions: column: Luna C-18, Gradient 20–50% B in 25 min, flow: 1 mL/min, 40° C., A-0.1% TFA in $H_2O$, B-0.1% TFA in $CH_3CN$, k': 7.94. Purity: >97% (215 nm), >97% (254 nm)

Example 3

Preparation of N,N-diethyl-4-[(5-hydroxy-2-iodophenyl)[1-(phenylmethyl)-4-piperidinyl]amino]-benzamide (compound 9).

To a suspension of the TFA salt (25 mg, 0.044 mmol) of the benzyl analogue 5 and (11.3 mg, 0.044 mmol) of silver triflate in 5 ml of $CH_2Cl_2$ at 0° C. was added dropwise a solution of 23 mg $I_2$ in 2 ml of $CH_2Cl_2$. When complete, the reaction was concentrated and purified by preparative HPLC. Yielded 7.9 mg.

Anal. Calcd for C29H34N3O2I×1.6 C2HO2F3×0.5 H2O: C, 49.91; H, 4.76; N, 5.42;

Found: C, 49.84.; H, 4.75; N, 5.60

M.S (calc'd): 584.51(NH+),

M.S (found): 584.16 (MH+)

HPLC Conditions: column: Zorbax SB–C18, Gradient 20–50% B in 25 min, flow 1 ml/min, 40 C, A-0.1% TFA in H2O, B-0.1% TFA in CH3CN, k': 8.56. Purity: >96% (215 nm), >96% (254 nm)

V. Synthesis of 2-fluro-5-methoxyaniline

Scheme III

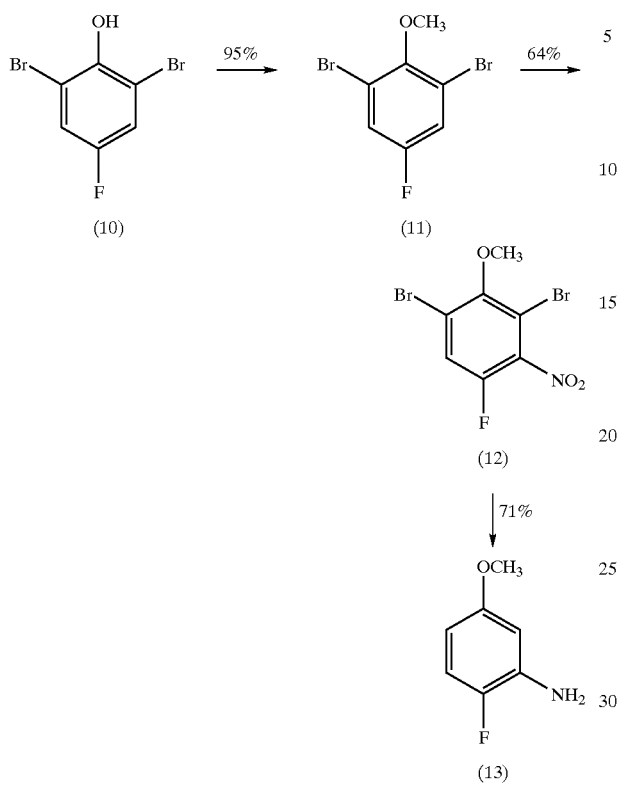

(i) Preparation of 1,3-dibromo-5-fluoro-2-methoxybenzene (compound 11).

To a solution of 10, 2,6-dibromo-4-flurophenol (1 g, 3.7 mmol), in 50 ml of acetone was added $K_2CO_3$ (0.56 g, 4.1 mmol) followed by $CH_3I$ (0.58 g, 255 µl, 4.1 mmol). The reaction was refluxed for 2 hrs, cooled then filtered and rinsed repeatedly with $CHCl_3$. The concentrated filtrate yielded 1 g of a cream coloured solid. 95.2%.

(ii) Preparation of 1,3-dibromo-5-fluoro-2-methoxy-4-nitro-benzene (compound 12).

To a cloudy solution of 11 (920 mg, 3.24 mmol) in 3 ml of $H_2SO_4$ cooled in ice was added dropwise a solution of $H_2SO/O_3$ (3 ml/163 µL, 3.9 mmol). The reaction was stirred for 2 hrs then 30 minutes at R/T. Ice was then added and the reaction extracted several times ch2cl2. The combined organic layers were washed with $Na_2CO_3$ (sat), dried over $Na_2SO_4$, filtered and concentrated. Purification over silica gel with 100 hexanes then 10% ethyl acetate/hexanes yielded 685 mg, 64%.

(iii) Preparation of 2-fluoro-5-methoxyaniline (compound 13).

In a Parr apparatus at 40 psi was shaken a suspension 66 mg of Pd/C 10% of 12 (670 mg, 0.2 mmol) in 40 ml of ethanol for 36 hrs. The reaction was filtered and the concentrated filtrate was purified by silica gel flash chromatography with increasing polarities of 10, 20 then 30 ethyl acetate/hexanes. Yield 200 mg, 70.8%.

Example 4

Preparation of 4-[(2,4-dibromo-5-methoxyphenyl)[1-(Phenylmethyl)-4-piperidinyl]amino]-N,N-diethyl-benzamide (compound 14)

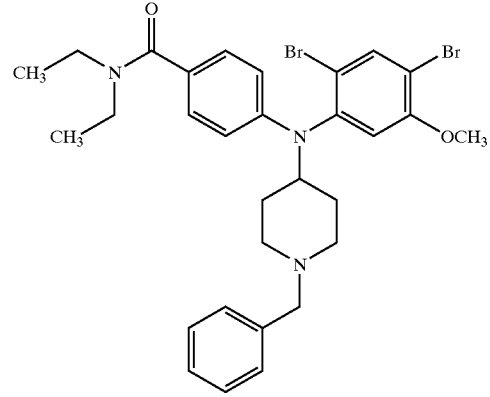

510 mg of compound 3 is dissolved in glacial acetic acid/$CH_2Cl_2$ at 0° C. 90 µl of bromine is added dropwise with stirring for 15 minutes. The reaction is concentrated taken into is $CH_2Cl_2$ and $H_2O$. The mixture is made basic with 2 N NaOH and extracted 3 times with $CH_2Cl_2$, then washed with brine. The compound was purified by preparative HPLC. The TFA salt was converted to the free amine (347 mg) by extraction with 1 N NaOH and $CH_2Cl_2$. The HCl was prepared from 1 N HCl in ether.

Anal. Calcd for C30H35N3O2Br2×1.5 HCl×0.7 $H_2O$: C, 51.72; H, 5.48; N, 6.03;
Found: C, 51.67; H, 5.50; N, 5.88
M.S (calc'd): 630.44(MH+),
M.S (found): 630.15 (MH+)
HPLC Conditions: column: Luna C-18, Gradient 30–50% B in 25 min, flow: 1 mL/min, 40° C., A-0.1% TFA in $H_2O$, B-0.1% TEA in $CH_3CN$, k': 3.25. Purity: >95% (215 nm), >99% (254 nm)

Example 5

Preparation of 4-[(2-chloro-5-hydroxyphenyl)[1-(phenylmethyl)-4-piperidinyl]amino]-N,N-diethyl-benzamide (compound 15)

The title compound 15 was prepared by following the synthetic procedure of Scheme I above, using 2-chloro-3-methoxyanaline in step 1.

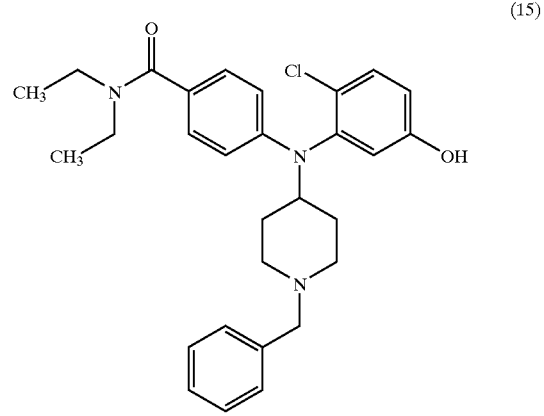

M.S (calc'd): 492.24 (MH+),
M.S (found): 491.92 (MH+)

HPLC Conditions: column: Luna C-18, Gradient 30–80% B in 25 min, flow: 1 mL/min, 25° C., A-0.1% TFA in H₂O, B-0.1% TFA in CH₃CN, k': 2.60. Purity: >90% (215 nm), >92% (254 nm)

Example 6

Preparation of N,N-diethyl-4-[(2-fluoro-5-hydroxyphenyl)[1-(phenylmethyl)-4-piperidinyl]amino]-benzamide (compound 16).

The title compound 16 was prepared by of Scheme I above, using 2-fluoro-3-methoxyanaline in step 1.

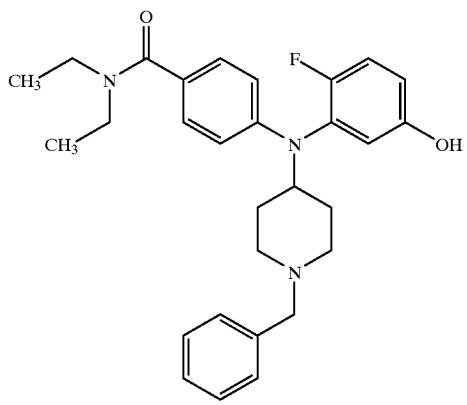

(16)

¹H NMR: CDCl3 d 1.15–1.19, (m, 6H), 1.49–1.57, (m, 2H), 1.87–1.90 (m, 2H), 2.12–2.19 (m, 2H), 2.97–3.01 (m, 2H), 3.42 (br s, 4H), 3.53 (s, 2H), 3.80–3.55 (m, 2H), 6.27–6.29 (m, 1H), 6.45 (d, J=8.7 Hz, 2H) 6.51–6.55 (m, 1H), 6.89 (t, 1H), 7.20 (d, J=8.7 Hz, 2H), 7.24–7.27 (m, 5H).

IR: 3160.1, 2936.0, 1602.6, 1502.1, 1472.0, 1456.3, 1283.3

M.S (calc'd): 476.61 (MH+),

M.S (found): 476.16 (MH+)

HPLC Conditions: column: Zorbax SB–C18, Gradient 30–80% B in 25 min, flow: 1 mL/min, 40 C, A-0.1% TFA in H₂O, B-0.1% TFA in CH3CN, k': 6.61. Purity: >99% (215 nm), >99% (254 nm)

Example 7

Preparation of 4-[(4-bromo-3-methoxyphenyl)[1-(phenylmethyl)-4-piperidinyl]amino]-N,N-diethyl-benzamide (compound 17)

The title compound 17 was prepared by of Scheme I above, using 2-bromo-3-methoxyanaline in step 1.

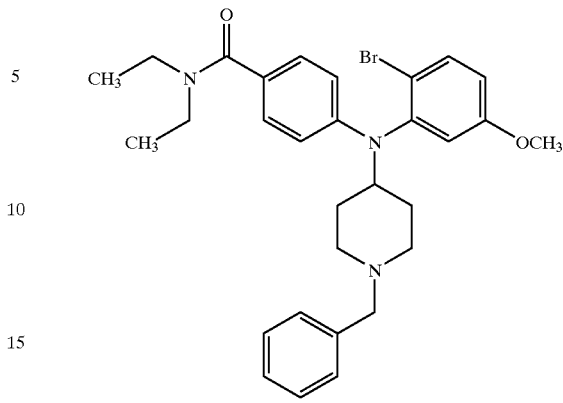

(17)

¹H NMR: CDCl3 d 1.16, (br t, 6H), 1.43–1.53, (m, 2H), 1.86–1.89 (m, 2H), 2.06–2.11 (m, 2H), 2.91–2.94 (m, 2H), 3.38 (br s, 4H), 3.37 (s, 2H), 3.46 (s, 2H), 3.75 (s, 3H), 3.77–3.83 (m, 1H), 6.44–6.46 (m, 2H), 6.63 (d, J=8.8 hz, 2H), 7.19–7.27 (m, 7H), 7.44 (d,1 H)

Anal. Calcd for C30H36N3O2Br×1.9 HCl×0.2 H2O: C, 57.80; H, 6.19; N, 6.74;
Found: C, 57.83; H, 6.17; N, 7.16.
M.S (calc'd): 551.54(MH+),
M.S (found): 550.39, 552.38 (MH+, brominated compound)

HPLC Conditions: column: Luna C-18, Gradient 20–50% B in 25 min, flow: 1 mL/min, 40° C., A-0.1% TFA in H₂O, B-0.1% TFA in CH₃CN, k': 5.05. Purity: >99% (215 nm), >99% (254 nm)

Example 8

Preparation of (1R)-N-[4-[(1-iminoethyl)amino]-(1R)-[[(1,2,3,4-tetrahydro-1-naphthalenylamino]carbonyl]butyl)-1-(phenyl)-cyclohexylcarboxamide (compound 18)

The title compound 18 was prepared by following the procedure of Scheme I above, using 2-chloro-3-methoxyanaline in step 1.

(18)

M.S (calc'd): 507.
M.S (found): 505.91. 507.85 (MH+, chlorinated compound)

HPLC Conditions: column: Luna C-18, Gradient 30–80% B in 25 min, flow: 1 mL/min, 40° C., A-0.1% TFA in H₂O, B-0.1% TFA in CH₃CN, k': 4.06. Purity: >88% (215 nm), >90% (254 nm)

Example 9
Preparation of N,N-diethyl-4-[(2-fluoro-5-methoxyphenyl)[1-(phenylmethyl)-4-piperidinyl]amino]-benzamide (Compound 19)

The title compound 19 was prepared by of Scheme I above, using 2-fluoro-3-methoxyanaline in step 1.

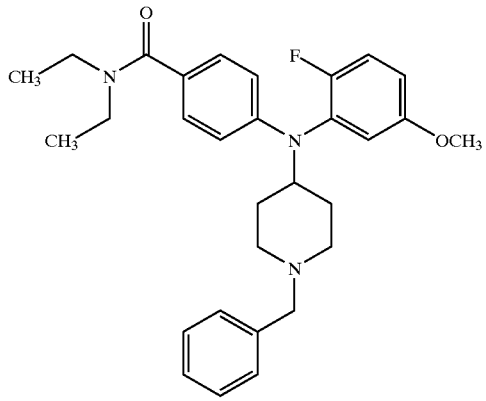

(19)

$^1$H NMR: CDCl3 d 1.15–1.18, (m, 6H), 1.50–1.59, (m, 2H), 1.96–1.99 (m, 2H), 2.09–2.15 (m, 2H), 2.95–2.98 (m, 2H), 3.42 (br s, 4H), 3.50 (s, 2H), 3.77 (s, 3H), 3.84–3.90 (m, 2H) 6.27–6.29 (m, 1H), 6.51 (d, J=8.9 Hz, 2H) 6.6 (dd, J=3.3 Hz, 6.3 Hz 1H), 7.08 (dt, J=3.4 Hz, 8.9 Hz, 1H), 7.08 (t, J=9.0 Hz, 21), 7.22 (d, J=8.9 Hz, 2H) 7.24–7.32 (m, 5H).

M.S (calc'd): 490.63 (MH+),
M.S (found): 490.08 (MH+)

HPLC Conditions: column: Luna C-18; gradient 30–80% B in 25 min, flow: 1 mL/min, 40 C, A-0.1% TFA in H$_2$O, B-0.1% TFA in CH3CN, k': 4.61. Purity: >99% (215 nm), >99% (254 nm)

Example 10
Preparation of N,N-diethyl-4-[[1(3-furanylmethyl)-4-piperidinyl](3-methoxyphenyl)amino]-benzamide (compound 20)

The title compound 20 was prepared by of Scheme I above, using furan-3-carboxaldehyde.

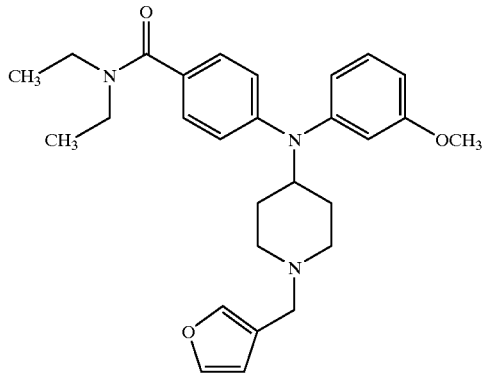

(20)

$^1$H NMR: CDCl3 d 1.18, (t, 6H), 1.48–1.58, (m, 2H), 1.92–1.96 (m, 2H), 2.06–2.12 (m, 2H), 2.96–2.99 (m, 2H), 3.37 (s, 2H), 3.42 (br s, 4H), 3.50 (s, 2H), 3.77 (s, 3H), 3.79–3.86 (m, 1H), 6.34 (s, 1H), 6.51–6.52 (m, 1H) 6.55–6.57 (m, 1H), 6.64–6.66 (m, 2H), 6.73 (dd, J=2.4, 8.1 Hz, 1H), 7.23–7.26 (m, 3H) 7.31 (s, 1H), 7.36–7.37 (m, 1H)

IR: 2935.4, 1611.0, 1595.4, 1469.4, 1425.6, 1280.7

M.S (calc'd): 462.60(MH+),

M.S (found): 462.21 (MH+)

HPLC Conditions: column: Luna C-18; gradient: 20–50% B in 25 min, 1 mL/min, 25° C., A-0.1% TFA in H$_2$O, B-0.1% TFA in CH3CN; k': 7.5; Purity: >99% (215 nm), >99% (254 nm)

Example 11

Preparation of N,N-diethyl-4-[[1-(2-furanylmethyl)-4-piperidinyl](3-methoxyphenyl)amino]-benzamide (compound 21)

The title compound 21 was prepared by of Scheme I above, using furan-2-carboxaldehyde.

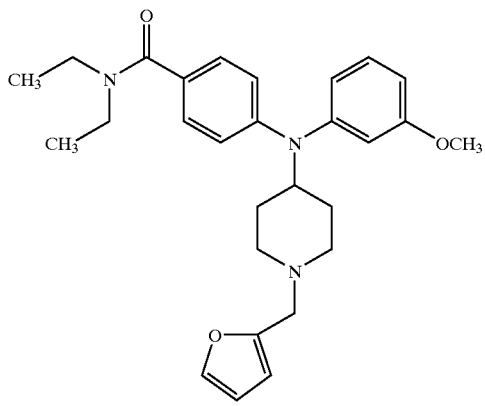

(21)

$^1$H NMR: CDCl3 d 1.19, (t, 6H), 1.54–1.64, (m, 2H), 1.92–1.96 (m, 2H), 2.13–2.19 (m, 2H), 2.96–2.99 (m, 2H), 3.42 (br s, 4H), 3.53 (s, 2H), 3.76 (s, 3H), 3.80–3.86 (m, 1H), 6.18 (d, J=Hz, 1H), 6.31 (dd, J=2.1 Hz, 3.3 Hz, 1H) 6.49–6.51 (m, 1H), 6.53–6.56 (m, 1H), 6.71 (d, 8.4 Hz, 2H) 6.73 (dd, J=2.5, 8.2 Hz, 1H), 7.23–7.26 (m, 3H) 7.36–7.37 (m,1H)

IR: 2935.5, 1611.3, 1595.2, 1469.0, 1424.6, 1280.6

M.S (calc'd): 462.60(MH+),

M.S (found): 462.21 (MH+)

Anal. Calcd for C28H36N3O3×1.7HCl×0.3H$_2$O: C, 63.58; H, 7.11; N, 7.94; Found: C, 63.70; H, 7.04; N, 7.84.

HPLC Conditions: column: Luna C-18; Gradient 20–50% B in 25 min; flow: 1 mL/min, 25° C., A-0.1% TFA in H2O, B-0.1% TFA in CH$_3$CN, k': 7.19. Purity: >95% (215 nm), >99% (254 nm)

Example 12

Preparation of N,N-diethyl-4-[(3-methoxyphenyl)[1-(3-thienylmethyl)-4-piperidinyl]amino]-benzamide (compound 22)

The title compound 22 was prepared by of Scheme I above, using thiophene-3-carboxaldehyde.

(22)

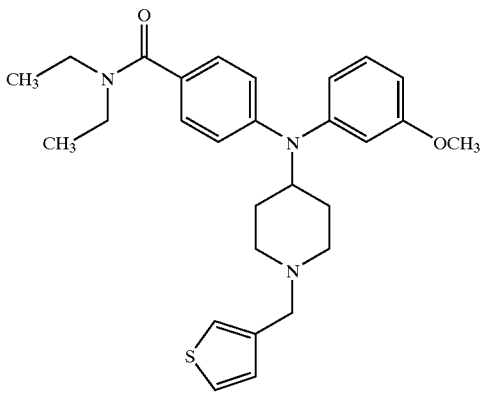

¹H NMR: CDCl3 d 1.18, (t, 6H), 1.52–1.58, (m, 2H), 1.92–1.95 (m, 2H), 2.08–2.13 (m, 2H) 2.95–2.98 (m, 2H), 3.42 (br s, 4H), 3.53 (s, 2H), 3.77 (s, 3H), 3.79–3.86 (m, 1H), 6.51–6.52 (m, 1H) 6.55–6.57 (m, 1H), 6.65 (d, J=8.5 Hz, 2H), 6.72–6.74 (m, 1H), 7.00–7.01 (m, 1H), 7.08–7.09 (m, 1H), 7.24–7.26 (m, 4H)

IR: 2936.1, 1611.1, 1595.6, 1469.4, 1425.1, 1280.6

M.S (calc'd): 478.67(MH+),

M.S (found): 478.07 (MH+)

HPLC Conditions: column: Luna C-18; gradient: 20–50% B in 25 min, 1 mL/min, 25° C., A-0.1% TFA in H2O, B-0.1% TFA in CH3CN; k': 7.0; Purity: >99% (215 nm), >99% (254 nm)

Example 13

Preparation of N,N-diethyl-4-[(3-methoxyphenyl)[1-(2-thienylmethyl)-4-piperidinyl]amino]-benzamide (compound 23)

The title compound 23 was prepared by of Scheme I above, using thiophene-2-carboxaldehyde.

(23)

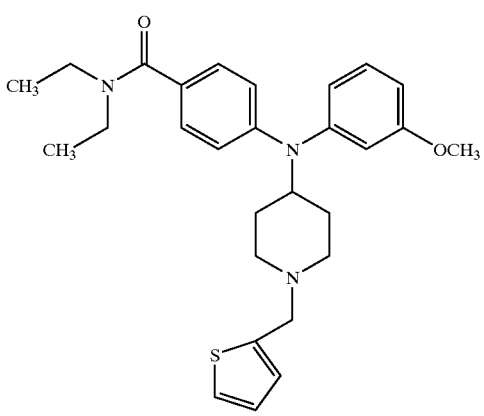

M.S (calc'd): 477.67(MH+),

M.S (found): 478.09 (MH+)

HPLC Conditions: column: Luna C-18; gradient: 20–50% B in 25 min, 1 mL/min, 25° C., A-0.1% TFA in H2O, B-0.1% TFA in CH3CN; k': 7.64; Purity: >99% (215 nm), >99% (254 nm)

Example 14

Preparation of N,N-diethyl-4-[[1-(1H-imidazol-2-ylmethyl)-4-piperidinyl](3-methoxyphenyl)amino]-benzamide (compound 24)

The title compound 24 was prepared by of Scheme I above, using imidazole-2-carboxaldehyde.

(24)

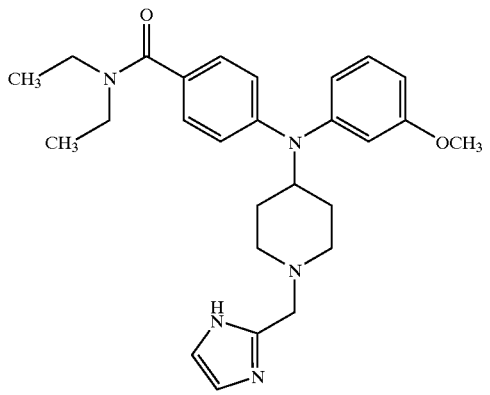

¹H NMR: CDCl3 d 1.18, (t, 6H), 1.46–1.55, (m, 2H), 1.95–1.97 (m, 2H), 2.24–2.30 (m, 2H), 2.88–2.91 (m, 2H), 3.43 (br s, 4H), 3.63 (s, 2H), 3.50 (s. 2H), 3.78 (s, 3H), 3.88–3.92 (m, 2H), 6.50 (t, 1H), 6.54–6.57 (m, 1H), 6.71 (d, J=Hz, 2H), 6.74 (dd, 2.3 Hz, 8.3 Hz, 1H) 6.96 (s, 2H), 7.24–7.29 (m, 3H)

IR: 2935.6, 1615.0, 1601.8, 1503.4, 1469.8, 1454.2, 1425.2, 1281.4

M.S (calc'd): 462.61 (MH+),

M.S (found): 462.10 (NM+)

HPLC Conditions: column: Luna C-18; gradient: 20–50% B in 25 min, 1 mL/min, 25° C., A-0.1% TFA in H2O, B-0.1% TFA in CH3CN; k': 4.9; Purity: >99% (215 nm), >99% (254 nm)

Example 15

Preparation of N,N-diethyl-4-[[1-(3-furanylmethyl)-4-piperidinyl](3-hydroxyphenyl)amino]-benzamide (Compound 25)

The title compound 25 was prepared by of Scheme I above, using furan-3-carboxaldehyde.

¹H NMR: CDCl3 d 1.17–1.20, (m, 6H), 1.54–1.63, (m, 2H), 1.90–1.93 (m, 2H), 2.12–2.17 (m, 2H), 3.02–3.05 (m, 2H), 3.42 (br s, 6H), 3.42 (br s, 4H), 3.80–3.86 (m, 1H), 6.29–6.30 (m, 1H), 6.35–6.37 (m, 1H) 6.47–6.50 (m, 1H), 6.53–6.56 (m, 1H), 6.60–6.63 (m, 2H), 7.12–7.22 (m, 1H) 7.23–7.28 (s, 4H), 7.28–7.34 (m, 1H)

M.S (calc'd): 448.58(MH+),

M.S (found): 448.21 (MH+)

HPLC Conditions: column: Luna C-18; gradient: 20–50% B in 25 min, 1 mL/min, 25° C., A-0.1% TFA in H2O, B-0.1% TFA in CH3CN; k': 5.53; Purity: >99% (215 nm), >99% (254 nm)

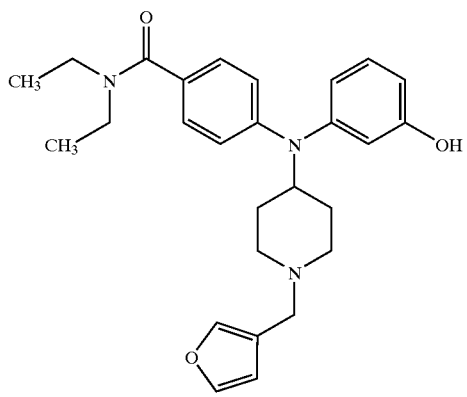

(25)

Example 16

Preparation of N,N-diethyl-4-[(3-hydroxyphenyl)[1-(3-thienylmethyl)-4-piperidinyl]amino]-benzamide (compound 26)

The title compound 26 was prepared by of Scheme I above, using thiophene-3-carboxaldehyde.

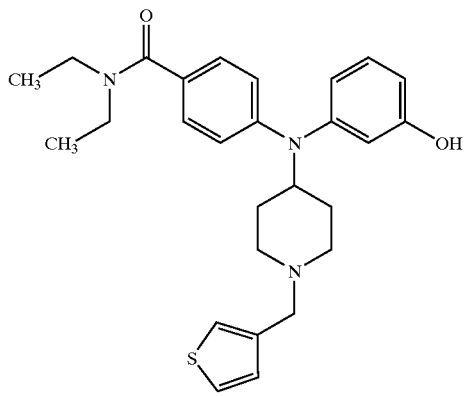

(26)

M.S (calc'd): 464.64 (MH+),

M.S (found): 464.15 (MH+)

HPLC Conditions: column: Luna C-18; gradient: 20–50% B in 25 min, 1 mL/min, 25° C., A-0.1% TFA in H$_2$O, B-0.1% TFA in CH3CN; k': 7.64; Purity: >99% (215 nm), >99% (254 nm)

Example 17

Preparation of N,N-diethyl-4-[(5-methoxy-2-methylphenyl) [1-(Phenylmethyl)-4-piperidinyl]amino]-benzamide (compound 27)

The title compound 27 was prepared by of Scheme I above, using 2-methyl-5-methoxyanaline in step 1.

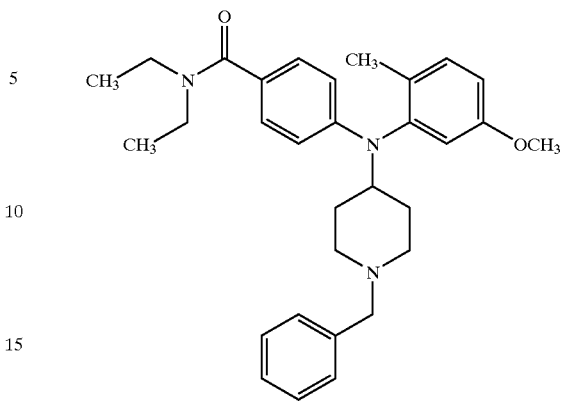

(27)

M.S (calc'd): 486.67(MH+),

M.S (found): 486.19 (MH+)

HPLC Conditions: column: Luna C-18; gradient: 20–50% B in 25 min, 1 mL/min, 25° C., A-0.1% TFA in H$_2$O, B-0.1% TFA in CH3CN; k': 8.46; Purity: >99% (215 nm), >99% (254 nm)

Example 18

Preparation of N,N-diethyl-4-[(3-hydroxyphenyl)[1-[[4-(trifluoromethyl)phenyl]methyl]-4-piperidinyl]amino]-benzamide (compound 28)

The title compound 28 was prepared by of Scheme I above, using 4-trifluoromethylbenzaldehyde.

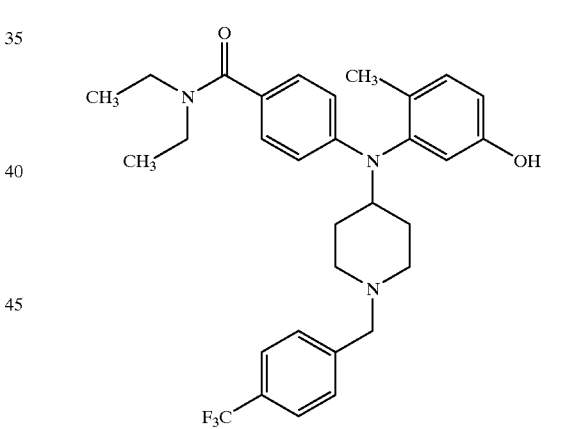

(28)

Anal. Calcd for C30H34N3O2F3×1.4 CF3CO2H: C, 57.34; H, 5.22; N, 6.12; Found: C, 57.31; H, 5.18; N, 6.23.

M.S (calc'd): 526.61 (MH+),

M.S (found): 526.29 (MH+)

HPLC Conditions: column: Zorbax SB C-18, Gradient 30–80% B in 25 min, flow: 1 mL/min, 40° C., A-0.1% TFA in H$_2$O, B-0.1% TFA in CH$_3$CN, k': 3.29. Purity: >96% (215 nm), >98% (254 nm)

Example 19

Preparation of N,N-diethyl-4-[(3-hydroxyphenyl)[1-[(4-iodophenyl)methyl]-4-piperidinyl]amino]-benzamide (compound 29)

The title compound 29 was prepared by of Scheme I above, using 4-iodobenzaldehyde.

(29)

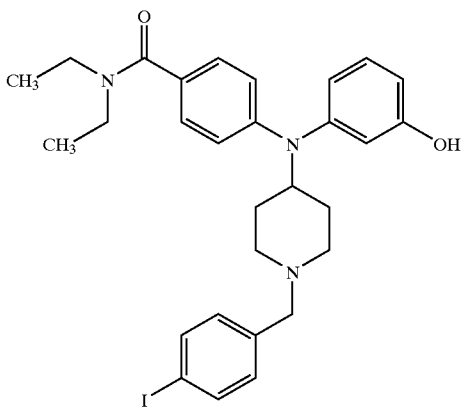

*¹H NMR: CDCl3 d 1.16, (br s, 6H), 1.88–2.06, (br m, 6H), 2.78–2.84 (m, 2H), 3.40–3.43 (m, 4H), 3.39–3.49 (br m, 4H), 3.92 (m, 1H), 4.12 (s, 2H), 4.32 (s, 2H), 6.54 (d, J=8.8 Hz, 2H), 6.61 (s, 1H), 6.71 (d, J=7.7 Hz, 2H), 7.44 (d, J=7.7 Hz, 2H), 7.13 (t, 1H), 7.36–7.45 (m, 5H)

Anal. Calcd for C29H34N3O2I×1.5 C2HO2F3×0.1 H$_2$O: C, 50.82; H, 4.76; N, 5.56;

Found: C, 50.79; H, 4.77; N, 5.62.

M.S (calc'd): 584.51 (MH+),

M.S (found): 584.14 (MH+)

HPLC Conditions: column: Zorbax SB C-18, Gradient 20–50% B in 25 min, flow: 1 mL/min, 40° C., A-0.1% TFA in H$_2$O, B-0.1% TFA in CH$_3$CN, k': 7.96. Purity: >98% (215 nm), >98% (254 nm)

Example 20

Preparation of N,N-diethyl-4-[[1-[(4-bromophenyl)methyl]-4-piperidinyl](3-hydroxyphenyl)amino]-benzamide (compound 30)

The title compound 30 was prepared by of Scheme I above, using 4-bromobenzaldehyde.

(30)

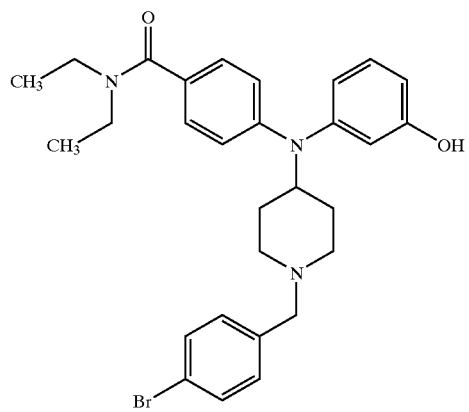

Anal. Calcd for C29H34BrN3O2×1.30 TFA Calc.: C 55.43%, H 5.20%, N 6.14%; Found: C 55.43%, H 5.25%, N 5.94%.

M.S (calc'd): 537.51 (MH+),

M.S (found): 536.54 (MH+), 538.04 (bromine compound)

HPLC Conditions: column: Zorbax SB C-18, Gradient 20–50% B in 25 min, flow: 1 mL/min, 40° C., A-0.1% TFA in H$_2$O, B-0.1% TFA in CH$_3$CN, k': 7.58. Purity: >99% (215 nm), >99% (254 nm)

Example 21

Preparation of N,N-diethyl-4-[[1-[(4-chlorophenyl)methyl]-4-piperidinyl](3-hydroxyphenyl)amino]-benzamide (compound 31)

The title compound 31 was prepared by of Scheme I above, using 4-chlorobenzaldehyde.

(31)

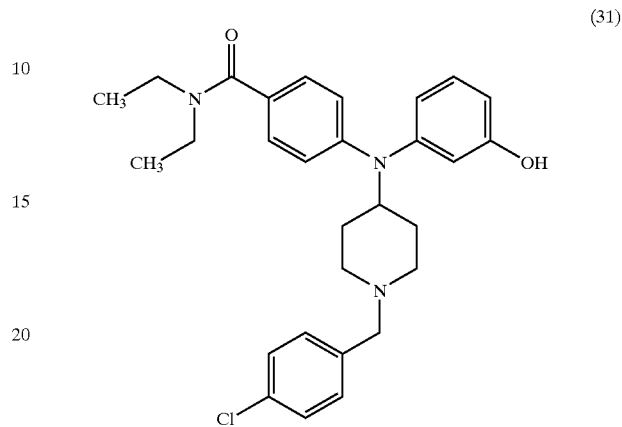

Anal. Calcd for C29H34N3O2Cl×1.4 CF3CO2H×0.3 H$_2$O: C, 57.64; H, 5.43; N, 6.34; Found: C, 57.49; H, 5.36; N, 6.41

M.S (calc'd): 496.06 (MH+),

M.S (found): 496.68 (MH+)

HPLC Conditions: column: Zorbax SB C-18, Gradient 20–50% B in 25 min, flow: 1 mL/min, 40° C., A-0.1% TFA in H$_2$O, B-0.1% TFA in CH$_3$CN, k': 7.36. Purity: >99% (215 nm), >98% (254 nm)

Example 22

Preparation of N,N-diethyl-4-[[1-[(4-fluorophenyl)methyl]-4-piperidinyl](3-hydroxyphenyl)amino]-benzamide (compound 32)

The title compound 32 was prepared by of Scheme I above, using 4-fluorobenzaldehyde.

(32)

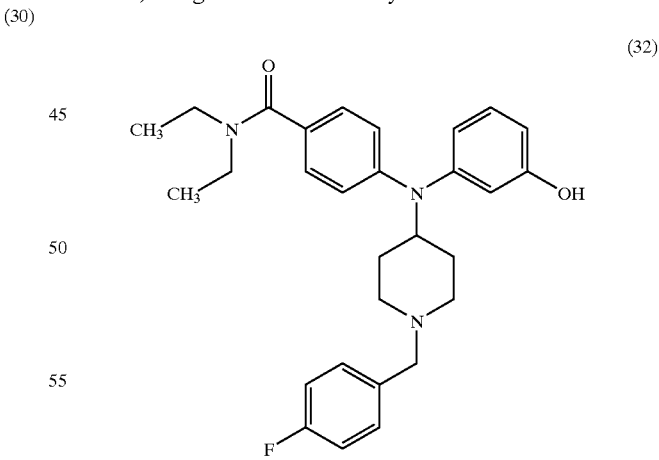

Anal. Calcd for C29H34FN3O2×1.90 TFA: C 56.91%, H 5.23%, N 6.07%; Found: C 56.77%, H 5.39%, N 5.95%, M.S (calc'd): 476.61 (MH+), M.S (found): 476.18 (MH+)

HPLC Conditions: column: Zorbax SB C-18, Gradient 20–50% B in 25 min, flow: 1 mL/min, 40° C., A-0.1% TFA in H$_2$O, B-0.1% TFA in CH$_3$CN, k': 2.45. Purity: >91% (215 nm), >96% (254 nm)

Example 23
Preparation of 4-[[1-[(2,4-dichlorophenyl)methyl]-4-piperidinyl](3-hydroxyphenyl)amino]-N,N-diethyl-benzamide (compound 33)

The title compound 33 was prepared by of Scheme I above, using 2,4-dichlorolbenzaldehyde.

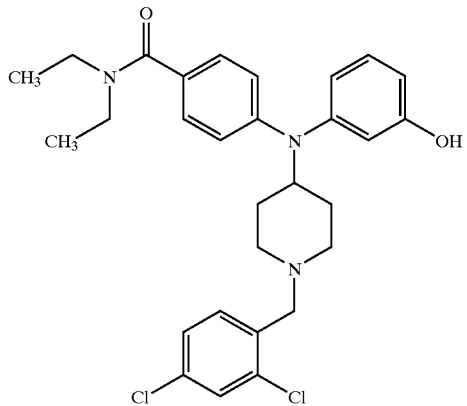

Anal. Calcd for C29H33Cl2N3O2, ×0.10 H$_2$O, ×1.60 TFA: C 54.42%, H 4.94%, N 5.91% Found: C 54.46%, H 4.94%, N 5.83%, M.S (calc'd): 527.51 (MH+),
M.S (found): 527.84 (NM+)

HPLC Conditions: column: Zorbax SB C-18, Gradient 20–50% B in 25 min, flow: 1 mL/min, 40° C., A-0.1% TFA in H$_2$O, B-0.1% TFA in CH$_3$CN, k': 8.14. Purity: >99% (215 nm), >99% (254 nm)

Example 24
Preparation of N,N-diethyl-4-[[1-[(3-fluorophenyl)methyl]-4-piperidinyl](3-hydroxyphenyl)amino]-benzamide (compound 34)

The title compound 34 was prepared by of Scheme I above, using 3-fluorobenzaldehyde.

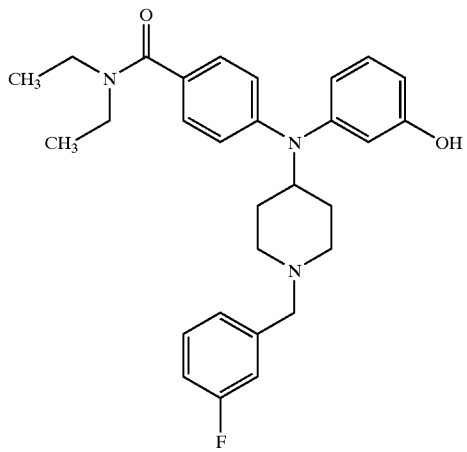

Anal. Calcd for C29H34N3O2F×1.2 C2HO2F3×1.1 H2O: C, 59.56; H, 6.11; N, 6.64;

Found: C, 59.43.; H, 5.48; N, 6.54.
M.S (calc'd): 476.61 (MH+),
M.S (found): 476.18 (MH+)

HPLC Conditions: column: Zorbax SB C-18, Gradient 20–50% B in 25 min, flow: 1 mL/min, 40° C., A-0.1% TFA in H$_2$O, B-0.1% TFA in CH$_3$CN, k': 6.53. Purity: >99% (215 nm), >99% (254 nm)

Example 25
Preparation of N,N-diethyl-4-[[1-[(2-fluorophenyl)methyl]-4-piperidinyl](3-hydroxyphenyl)amino]-benzamide (compound 35)

The title compound 35 was prepared by of Scheme I above, using 2-fluorobenzaldehyde.

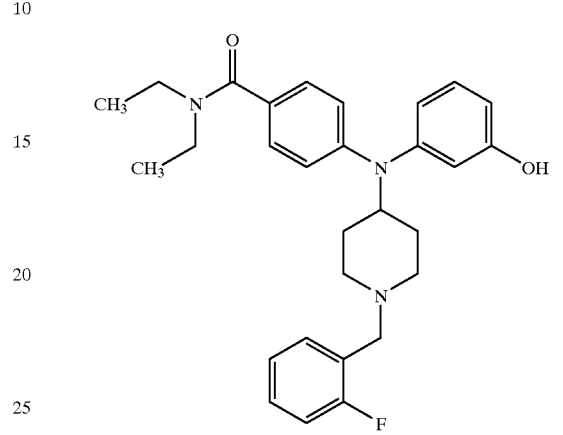

Anal. Calcd for C29H34N3O2F×1.4 C2HO2F3: C, 60.09; H, 5.62; N, 6.61; Found C, 60.09; H, 5.59; N, 6.62.

M.S (calc'd): 476.61 (MH+),
M.S (found): 476.18 (MH+)

HPLC Conditions: column: Zorbax SB C-18, Gradient 20–50% B in 25 min, flow: 1 mL/min, 40° C., A-0.1% TFA in H$_2$O, B-0.1% TFA in CH$_3$CN, k': 5.63. Purity: >99% (215 nm), >99% (254 nm)

Example 26
Preparation of N,N-diethyl-4-[(3-hydroxyphenyl)[1-[(4-methylphenyl)methyl]-4-piperidinyl]amino]-benzamide (compound 36)

The title compound 36 was prepared by of Scheme I above, using 4-methylbenzaldehyde.

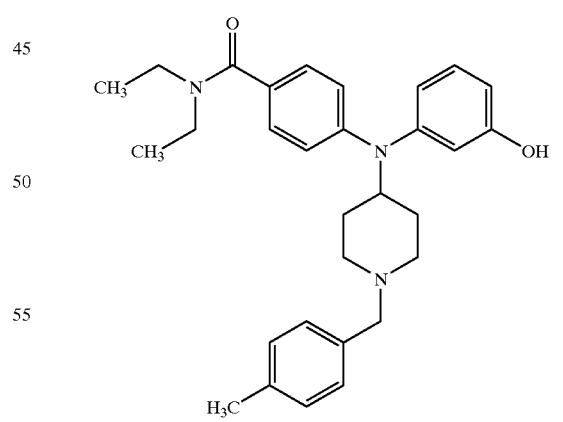

Anal. Calcd for C30H37N3O2×1.4 C2HO2F3×0.4 H$_2$O: C, 61.70; H, 6.19; N, 6.58;

Found: C, 61.78.; H, 6.25; N, 6.55.
M.S (calc'd): 472.64 (MH+),
M.S (found): 472.18 (MH+)

HPLC Conditions: column: Zorbax SB C-18, Gradient 20–50% B in 25 min, flow: 1 mL/min, 40° C., A-0.1% TFA in H₂O, B-0.1% TFA in CH₃CN, k': 7.12. Purity: >98% (215 nm), >98% (254 nm)

Example 27

Preparation of N,N-diethyl-4-[[1-(2-furanylmethyl)-4-piperidinyl](3-hydroxyphenyl)amino]-benzamide (compound 37)

The title compound 37 was prepared by of Scheme I above, using 2-furaldehyde.

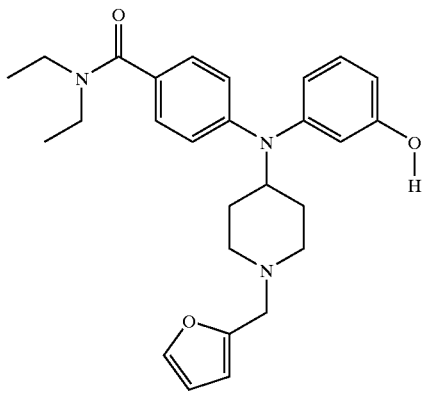

(37)

400 MHz, DMSO) d 1.07 (t, J=7.4 Hz, 6H, 2×CH3), 1.53–1.63 (m, 2H, 2×CH), 2.04–2.08 (m, 2H, 2×CH), 3.11–3.18 (m, 2×CH), 3.37–3.41 (m, 2×CH), 3.48 (Br, 2×CH2), 4.17–4.24 (m, 1H, NCH), 4.33 (s, 2H, NCH2), 6.36–6.38 (m, 1H), 6.44–6.46 (m, 1H), 6.55–6.56 (m, 1H), 6.62–6.68 (m, 4H), 7.16–7.23 (m, 3H), 7.81 (m, 1H), 9.53 (br, 1H)

Anal. Calcd for C27H33N3O3×1.3 C2HF3O2×1.0 H₂O: C, 58.09; H, 5.95; N, 6.87; Found: C, 58.03; H, 5.90; N, 6.94.

M.S (calc'd): 448.58(MH+),

M.S (found): 448.21 (MH+)

HPLC Conditions: column: Luna C-18; gradient: 20–50% B in 25 min, 1 mL/min, 25° C., A-0.1% TFA in H₂O, B-0.1% TFA in CH3CN; k': 2.83; Purity: >99% (215 nm), >99% (254 nm)

Example 28

Preparation of N,N-diethyl-4-[(3-hydroxyphenyl)[1-(2-thienylmethyl)-4-piperidinyl]amino]-benzamide (compound 38)

The title compound 38 was prepared by of Scheme I above, using 2-thiophencarboxaldehyde.

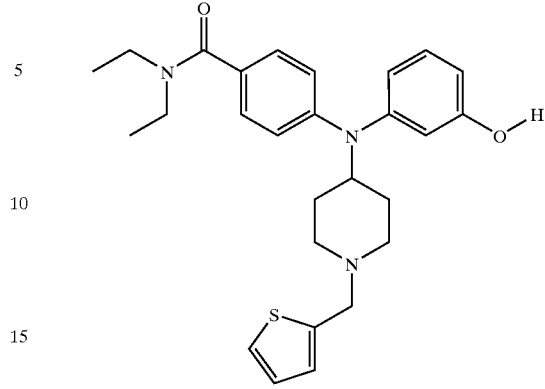

(38)

¹H NMR: (400 MHz, DMSO) d 1.18 (t, J=7.4 Hz, 6H, 2×CH3), 1.52–1.62 (m, 2H, 2×CH), 1.89–1.93 (m, 2H, 2×CH), 2.14–2.21 (m, 2×CH), 3.00–3.03 (m, 2×CH), 3.42 (Br, 2×CH2), 3.74 (s, 2H, NCH2), 3.80–3.83 (m, 1H, NCH), 6.33–6.35 (m, 1H), 6.47–6.49 (m, 1H), 6.56–6.59 (m, 1H), 6.62–6.65 (m, 2H), 6.89–6.94 (m, 2H), 7.13–7.17 (m, 1H), 7.20–7.22 (m, 1H), 7.22–7.26 (m, 2H)

¹H NMR: (Anal. Calcd for C₂₇H₃₃N₃O₂S×1.3 C2HF3O2×0.5 H₂O: C, 57.26; H, 5.73; N, 6.77; Found: C, 57.32; H, 5.79; N, 6.73.

M.S (calc'd): 464.64 (MH+),

M.S (found): 464.15 (MH+)

HPLC Conditions: column: Luna C-18; gradient: 20–50% B in 25 min, 1 mL/min, 25° C., A-0.1% TFA in H₂O, B-0.1% TFA in CH3CN; k': 5.99; Purity: >99% (215 nm), >99% (254 nm)

Example 29

Preparation of N,N-diethyl-4-{3-hydroxy[1-(1H-imidazol-2-ylmethyl)-4-piperidinyl]anilino}benzamide (compound 39)

The title compound 39 was prepared by of Scheme I above, using 2-imidazolecarboxaldehyde.

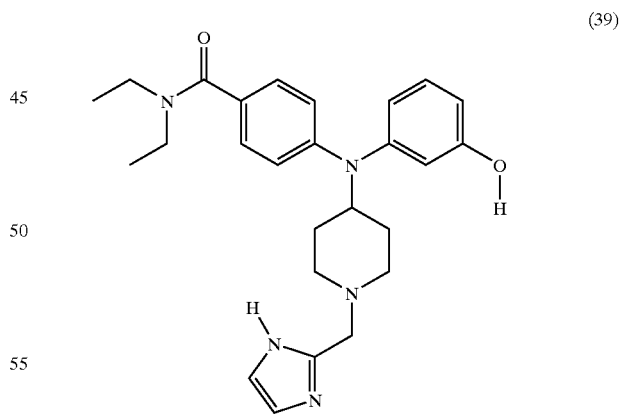

(39)

¹H NMR: (400 MHz, DMSO) δ 1.08 (t, 6H, 2×CH3), 1.54–1.63 (m, 2H, 2×CH), 2.04–2.08 (m, 2H, 2×CH), 3.09–3.17 (m, 2× CH), 3.27–3.33 (m, 2×CH2), 3.40–3.45 (2×CH), 4.16–4.22 (m, 3H, NCH, NCH2), 6.38 (s, 1H), 6.45–6.48 (m, 1H), 6.64 (d, J=8.4 Hz, 2H), 6.66–6.69 (m, 1H), 7.18 (d, J=8.4 Hz, 2H), 7.20–7.22 (m, 1H), 7.48 (s 1H), 8.28

Anal. Calcd for C26H33N5O2×2.0 C2HF3O2×1.1 H₂O: C, 51.81; H, 5.39; N, 10.07;

Found: C, 51.87; H, 5.40; N, 10.01.

M.S (calc'd): 448.58 (MH+),

M.S (found): 448.22 (MH+)

HPLC Conditions: column: Luna C-18; gradient: 20–50% B in 25 min, 1 mL/min, 25° C., A-0.1% TFA in $H_2O$, B-0.1% TFA in CH3CN; k': 2.92; Purity: >99% (215 nm), >99% (254 nm)

Example 30

Preparation of N,N-diethyl-4-{3-hydroxy[1-(2-pyridinylmethyl)-4-piperidinyl]anilino}benzamide (compound 40)

The title compound 40 was prepared by of Scheme I above, using 2-pyridinecarboxaldehyde.

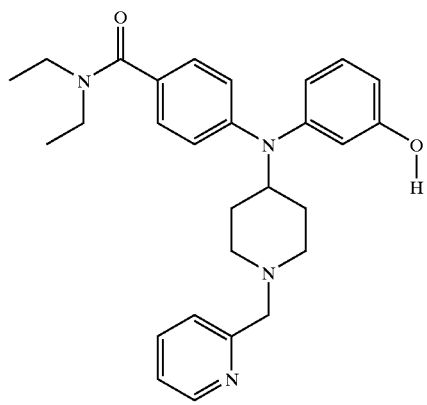

(40)

$^1$H NMR: (400 MHz, DMSO) δ 1.07 (t, 6H, 2×CH3), 1.66–1.75 (m, 2H, 2×CH),2.01–2.05 (m, 2H, 2×CH), 3.21–3.46 (m, 8H, 2×CH, 2×CH2, 2×CH), 4.20–4.23 (m, 1H, NCH), 4.39 (s, 2H, NCH2), 6.37–39 (m, 1H), 6.45–6.48 (m, 1H), 6.64 (d, J=8.4 Hz, 2H), 6.66–6.68 (m, 1H), 7.18 Hz (d, J=8.4 Hz, 2H), 7.21–7.24 (m, 1H), 7.43–7.51 (m, 2H), 7.88–7.92 (s, 1H), 8.62–8.63 (m, 1H), 9.53 (br s, 1H), 9.69 (br s, 1H)

Anal. Calcd for C28H34N4O2×1.5 C2HF3O2×0.2 $H_2O$: C, 58.80; H, 5.71; N, 8.85;

Found: C, 58.78; H, 5.77; N, 8.74.

M.S (calc'd): 459.60 (MH+),

M.S (found): 459.23 (MH+)

HPLC Conditions: column: Luna C-18; gradient: 20–50% B in 25 min, 1 mL/min, 25° C., A-0.1% TFA in 1120, B-0.1% TFA in CH3CN; k': 4.89; Purity: >99% (215 nm), >99% (254 nm)

Example 31

Preparation of N,N-diethyl-4-{3-hydroxy[1-(1-H-imidazol-5-ylmethyl)-4-piperidinyl]anilino}benzamide (compound 41)

The title compound 41 was prepared by of Scheme I above, using 4-imidazolecarboxaldehyde.

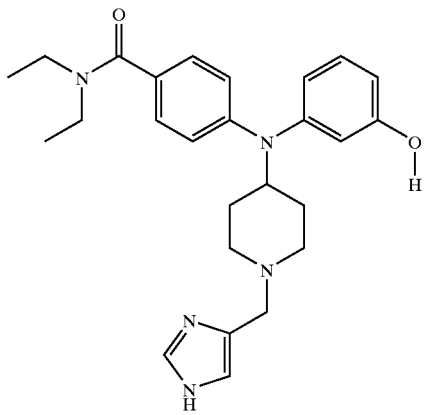

(41)

$^1$H NMR: (400 MHz, DMSO) δ 1.08 (t, 6H, 2×CH3), 1.54–1.63 (m, 2H, 2×CH), 2.04–2.08 (m, 2H, 2×CH), 3.09–3.17 (m, 2×CH), 3.27–3.33 (m, 2×CH2), 3.40–3.45 (2×CH), 4.16–4.22 (m, 3H, NCH, NCH2), 6.38 (s, 1H), 6.45–6.48 (m, 1H), 6.64 (d, J=8.4 Hz, 2H), 6.66–6.69 (m, 1H), 7.18 (d, J=8.4 Hz, 2H), 7.20–7.22 (m, 1H), 7.48 (s 1H), 8.28 (br s, 1H), 9.53 (br s, 1H)

Anal. Calcd for C26H33N5O2×2.3 C2HF3O2×0.8 $H_2O$: C, 50.75; H, 5.14; N, 9.67;

Found: C, 50.80; H, 5.15; N, 9.56.

M.S (calc'd): 448.58 (MH+),

M.S (found): 448.23 (MH+)

HPLC Conditions: column: Luna C-18; gradient: 20–50% B in 25 min, 1 mL/min, 25° C., A-0.1% TFA in H2O, B-0.1% TFA in CH3CN; k': 2.92; Purity: >99% (215 nm), >99% (254 nm)

Example 32

Preparation of N,N-diethyl-4-{3-hydroxy[1-(4-pyridinylmethyl)-4-piperidinyl]anilino}benzamide (compound 42)

The title compound 42 was prepared by of Scheme I above, using 4-pyridinecarboxaldehyde.

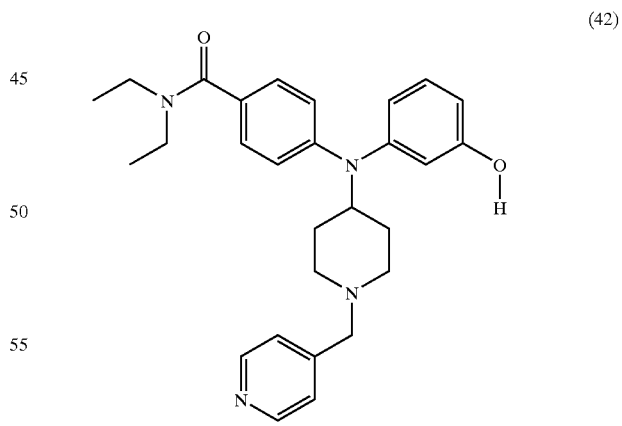

(42)

$^1$H NMR: (400 MHz, DMSO) δ 1.06 (t, 6H, 2×CH3), 1.53–1.62 (m, 2H, 2×CH), 2.04–2.08 (m, 2H, 2×CH), 3.15–3.21 (m, 2H, 2×CH), 3.26–3.31 (m, 4H, 2×CH2), 3.39–3.42 (m, 2H, 2×CH), 4.18–4.24 (m, 1H, NCH), 4.30 (s, 2H, NCH2), 6.36–39 (m, 1H), 6.44–6.47 (m, 1H), 6.62 (d, J=8.4 Hz, 21H), 6.66–6.689 (m, 1H), 7.18 Hz (d, J=8.4 Hz, 2H), 7.21–7.24 (m, 1H), 7.51 (d, J=5.6 Hz, 2H), 8.68 (d, J=5.6 Hz, 1H), 9.45 (br s, 1H)

Anal. Calcd for C28H34N4O2×2.4 C2HF3O2×1.1 H$_2$O: C, 52.38; H, 5.17; N, 7.45;
Found: C, 52.42; H, 5.27; N, 7.35.
M.S (calc'd): 459.60 (MH+),
M.S (found): 459.23 (MH+)
HPLC Conditions: column: Luna C-18; gradient: 20–50% B in 25 min, 1 mL/min, 25° C., A-0.1% TFA in H$_2$O, B-0.1% TFA in CH3CN; k': 3.07; Purity: >99% (215 nm), >99% (254 nm)

Example 33
Preparation of N,N-diethyl-4-(3-hydroxy{1-[(1-methyl-1H-imidazol-2-yl)methyl]-4-piperidinyl}anilino)benzamide (compound 43)

The title compound 43 was prepared by of Scheme I above, using 1-methyl-2-imidazolecarboxaldehyde.

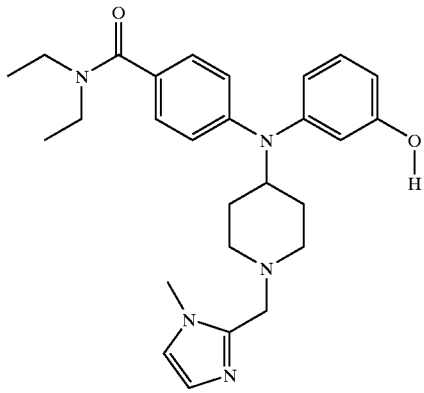

(43)

$^1$H NMR: (400 MHz, (CD3OD) δ 1.15–1.20 (m, 6H, 2×CH3), 1.57–1.67 (m, 2H, 2×CH), 2.02–2.08 (m, 2H, 2×CH), 2.59–2.66 (m, 2×CH), 3.03–3.09 (m, 2×CH), 3.44 (br s, 2×CH2), 3.83 (s, 3H, NCH3), 3.99 (Br s, NCH2), 4.01–4.09 (m, 1H, CH), 6.48–6.50 (m, 1H), 6.53–6.56 (m, 1H), 6.64–6.67 (m, 2H), 6.72–6.75 (m, 1H), 7.19–7.25 (m, 3H), 7.37 (m, 1H), 7.44 (m, 1H)
Anal. Calcd for C27H35N5O2×2.0 C2HF3O2×0.2 H$_2$O: C, 53.71; H, 5.44; N, 10.10;
Found: C, 53.67; H, 5.80; N, 10.20.
M.S (calc'd): 462.61 (MH+),
M.S (found): 462.23 (MH+)
HPLC Conditions: column: Luna C-18; gradient: 20–50% B in 25 min, 1 mL/min, 25° C., A-0.1% TPA in H2O, B-0.1% TFA in CH3CN; k': 3.07; Purity: >99% (215 nm), >99% (254 nm)

Pharmaceutical Compositions

The novel compounds according to the present invention may be administered orally, intramuscularly, subcutaneously, topically, intranasally, intraperitoneally, intrathoracially, intravenously, epidurally, intrathecally, intracerebroventricularly and by injection into the joints.

A preferred route of administration is orally, intravenously or intramuscularly.

The dosage will depend on the route of administration, the severity of the disease, age and weight of the patient and other factors normally considered by the attending physician, when determining the individual regimen and dosage level as the most appropriate for a particular patient.

For preparing pharmaceutical compositions from the compounds of this invention, inert, pharmaceutically acceptable carriers can be either solid or liquid. Solid form preparations include powders, tablets, dispersible granules, capsules, cachets, and suppositories.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active component is mixed with the carrier having the necessary binding properties in suitable proportions and compacted in the shape and size desired.

For preparing suppository compositions, a low-melting wax such as a mixture of fatty acid glycerides and cocoa butter is first melted and the active ingredient is dispersed therein by, for example, stirring. The molten homogeneous mixture is then poured into convenient sized molds and allowed to cool and solidify.

Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

Pharmaceutically acceptable salts are acetate, benzenesulfonate, benzoate, bicarbonate, bitartrate, bromide, calcium acetate, camsylate, carbonate, chloride, citrate, dihydrochloride, edetate, edisylate, estolate, esylate, fumarate, glucaptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate mesylate, methylbromide, methylnitrate, methylsulfate, mucate, napsylate, nitrate, pamoate (embonate), pantothenate, phosphate/diphosphate, polygalacturonate, salicylate, stearate, subacetate, succinate, sulfate, tannate, tartrate, teoclate, triethiodide, benzathine, chloroprocaine, choline, diethanolamine, ethylenediamine, meglumine, procaine, aluminium, calcium, lithium, magnesium, potassium, sodium, and zinc. Preferred pharmaceutically acceptable salts are the hydrochlorides, and bitartrates. The hydrochloride and sulphate salts are particularly preferred.

The term composition is intended to include the formulation of the active component with encapsulating material as a carrier providing a capsule in which the active component (with or without other carriers) is surrounded by a carrier which is thus in association with it. Similarly, cachets are included.

Tablets, powders, cachets, and capsules can be used as solid dosage forms suitable for oral administration.

Liquid from compositions include solutions, suspensions, and emulsions. Sterile water or water-propylene glycol solutions of the active compounds may be mentioned as an example of liquid preparations suitable for parenteral administration. Liquid compositions can also be formulated in solution in aqueous polyethylene glycol solution.

Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art.

Preferably the pharmaceutical compositions is in unit dosage form. In such form, the composition is divided into unit doses containing appropriate quantities of the active component. The unit dosage form can be a packaged preparation, the package containing discrete quantities of the preparations, for example, packeted tablets, capsules, and powders in vials or ampoules. The unit dosage form can also be a capsule, cachet, or tablet itself, or it can be the appropriate number of any of these packaged forms.

BIOLOGICAL EVALUATION

In vitro Model
Cell Culture

Human 293S cells expressing cloned human μ, δ, and κ receptors and neomycin resistance were grown in suspension at 37° C. and 5% $CO_2$ in shaker flasks containing calcium-free DMEM10% FBS, 5% BCS, 0.1% Pluronic F-68, and 600 μg/ml geneticin.

Membrane Preparation

Cells were pelleted and resuspended in lysis buffer (50 mM Tris, pH 7.0, 2.5 mM EDTA, with PMSF added just prior to use to 0.1 mM from a 0.1 M stock in ethanol), vortexed and incubated at 25° C. for 60–75 min, after which time the contents are rapidly vacuum-filtered and washed with about 12 ml/tube iced wash buffer (50 mM Tris, pH 7.0, 3 mM $MgCl_2$) through GF/B filters (Whatman) presoaked for at least 2 h in 0.1% polyethyleneimine. The radioactivity (dpm) retained on the filters was measured with a beta counter after soaking the filters for at least 12 h in minivials containing 6–7 ml scintillation fluid. If the assay is set up in 96-place deep well plates, the filtration is over 96-place PEI-soaked unifilters, which were washed with 3×1 ml wash buffer, and dried in an oven at 55° C. for 2 h. The filter plates were counted in a TopCount (Packard) after adding 50 μl MS-20 scintillation fluid/well. All biological data are tabulated in Table 1.

TABLE 1

Biological data for Examples recites in the specification.

| Example # | HDELTA HDELTA | HDELTA EC50 | HDELTA % EMAX | RAT BRAIN EC50 | RAT BRAIN % EMAX | MOUSE BRAIN EC50 | MOUSE BRAIN % EMAX | MLM 10000 % REM. | MLM 100000 % REM. | RLM 10000 % REM. | RLM 100000 % REM. |
|---|---|---|---|---|---|---|---|---|---|---|---|
| 1  | 0.436 | 0.61  | 105.4  | 9.61   | 99.49  | 14.97  | 112.07 | 10.4   | 85.2   | 4.333 | 66.125 |
| 6  | 0.466 | 0.21  | 107.1  | 3.41   | 133.06 | 3.54   | 134.25 | 2      | 69     | 5.333 | 81.333 |
| 15 | 0.221 | 0.22  | 104.82 | 4.29   | 140.11 | 7.5    | 131.28 | 3.5    | 83.5   | 8     | 73     |
| 16 | 0.271 | 0.22  | 96.86  | 5.53   | 123.99 | 7.92   | 140.7  | 5      | 83     | 1.5   | 66.5   |
| 19 | 1.296 | 1.26  | 103.63 | 50.48  | 88.32  |        |        | 30.667 | 61.667 | 0     | 35.667 |
| 20 | 1.324 | 0.98  | 99.86  | 36.88  | 86.02  | 20.72  | 74.02  | 30.5   | 81.5   | 4.5   | 51.5   |
| 21 | 0.987 | 1.52  | 98.72  | 81.24  | 101.79 |        |        | 16.333 | 85     | 2.333 | 45     |
| 22 | 2.127 | 1.23  | 109.06 | 19.03  | 102.46 | 23.98  | 96.36  | 8.5    | 85     | 17    | 63     |
| 23 | 1.436 | 0.4   | 98.85  | 6.83   | 102.98 | 4.74   | 91.08  | 30.5   | 93     | 20.5  | 75     |
| 24 | 0.704 | 2.63  | 92.31  | 45.93  | 92.88  | 43.21  | 91.26  | 3.5    | 71.5   | 3.5   | 87.5   |
| 25 | 0.763 | 1.13  | 111.21 | 14.4   | 113.59 | 16.14  | 112.12 | 0      | 71     | 4     | 71     |
| 26 | 0.641 | 1.14  | 104.65 | 11.72  | 78.42  | 9.3    | 88.34  | 31.5   | 86     | 3.5   | 63.5   |
| 27 | 0.416 | 1.29  | 101.34 | 19.64  | 129.03 | 44.19  | 130.03 | 2      | 65     | 3.5   | 54.5   |
| 28 | 0.651 | 0.7   | 106.46 | 23.45  | 141.23 | 40.24  | 144.02 | 1.5    | 80     | 1.5   | 52     |
| 29 | 0.3   | 1.17  | 118.27 | 18.68  | 107.04 | 31.03  | 130.01 | 6      | 92.5   | 36.5  | 74.5   |
| 30 | 0.24  | 0.26  | 95.88  | 4.12   | 158.09 | 6.55   | 159.09 | 26     | 82     | 31    | 74     |
| 31 | 1.61  | 14.05 | 105.52 | 130.53 | 41.3   | 152.57 | 50.26  |        |        |       |        |
| 32 | 1.023 | 3.92  | 114.6  | 85     | 122.51 | 119.46 | 115.43 |        |        |       |        |
| 33 | 1.707 | 13.3  | 87.74  | 125.51 | 100.37 | 217.34 | 100.53 |        |        |       |        | incubated on ice for 15 min, then homogenized with a polytron for 30 sec. The suspension was spun at 1000 g (max) for 10 min at 4° C. The supernatant was saved on ice and the pellets resuspended and spun as before. The supernatants from both spins were combined and spun at 46,000 g(max) for 30 min. The pellets were resuspended in cold Tris buffer (50 mM Tris/Cl, pH 7.0) and spun again. The final pellets were resuspended in membrane buffer (50 mM Tris, 0.32 M sucrose, pH 7.0). Aliquots (1 ml) in polypropylene tubes were frozen in dry ice/ethanol and stored at −70° C. until use. The protein concentrations were determined by a modified Lowry assay with SDS.

Binding Assays

Membranes were thawed at 37° C., cooled on ice, passed 3 times through a 25-gauge needle, and diluted into binding buffer (50 mM Tris, 3 mM $MgCl_2$, 1 mg/ml BSA (Sigma A-7888), pH 7.4, which was stored at 4° C. after filtration through a 0.22 m filter, and to which had been freshly added 5 μg/ml aprotinin, 10 μM bestatin, 10 μM diprotin A, no DTT). Aliquots of 100 μl (for μg protein, see Table 1) were added to iced 12×75 mm polypropylene tubes containing 100 μl of the appropriate radioligand (see Table 1) and 100 μl of test peptides at various concentrations. Total (TB) and nonspecific (S) binding were determined in the absence and presence of 10 μM naloxone respectively. The tubes were Data Analysis The specific binding (SB) was calculated as TB-NS, and the SB in the presence of various test peptides was expressed as percentage of control SB. Values of $IC_{50}$ and Hill coefficient ($n_H$) for ligands in displacing specifically bound radioligand were calculated from logit plots or curve fitting programs such as Ligand, GraphPad Prism, SigmaPlot, or ReceptorFit. Values of $K_i$ were calculated from the Cheng-Prussoff equation. Mean±S.E.M. values of $IC_{50}$, $K_i$ and $n_H$ were reported for ligands tested in at least three displacement curves.

Receptor Saturation Experiments

Radioligand Kδ values were determined by performing the binding assays on cell membranes with the appropriate radioligands at concentrations ranging from 0.2 to 5 times the estimated Kδ (up to 10 times if amounts of radioligand required are feasible). The specific radioligand binding was expressed as pmole/mg membrane protein. Values of Kδ and $B_{max}$ from individual experiments were obtained from non-linear fits of specifically bound (B) vs. nM free (F) radioligand from individual according to a one-site model.

Determination of Mechano-Allodynia Using Von Frey Testing

Testing was performed between 08:00 and 16:00 h using the method described by Chaplan et al. (1994). Rats were placed in Plexiglas cages on top of a wire mesh bottom which allowed access to the paw, and were left to habituate for 10–15 min. The area tested was the mid-plantar left hind paw, avoiding the less sensitive foot pads. The paw was touched with a series of 8 Von Frey hairs with logarithmically incremental stiffness (0.41, 0.69, 1.20, 2.04, 3.63, 5.50, 8.51, and 15.14 grams; Stoelting, Ill., USA). The von Frey hair was applied from underneath the mesh floor perpendicular to the plantar surface with sufficient force to cause a slight buckling against the paw, and held for approximately 6–8 seconds. A positive response was noted if the paw was sharply withdrawn. Flinching immediately upon removal of the hair was also considered a positive response. Ambulation was considered an ambiguous response, and in such cases the stimulus was repeated.

Testing Protocol

The animals were tested on postoperative day 1 for the FCA-treated group. The 50% withdrawal threshold was determined using the up-down method of Dixon (1980). Testing was started with the 2.04 g hair, in the middle of the series. Stimuli were always presented in a consecutive way, whether ascending or descending. In the absence of a paw withdrawal response to the initially selected hair, a stronger stimulus was presented; in the event of paw withdrawal, the next weaker stimulus was chosen. Optimal threshold calculation by this method requires 6 responses in the immediate vicinity of the 50% threshold, and counting of these 6 responses began when the first change in response occurred, e.g. the threshold was first crossed. In cases where thresholds fell outside the range of stimuli, values of 15.14 (normal sensitivity) or 0.41 (maximally allodynic) were respectively assigned. The resulting pattern of positive and negative responses was tabulated using the convention, X=no withdrawal; O=withdrawal, and the 50% withdrawal threshold was interpolated using the formula:

$$50\% \text{ g threshold} = 10^{(Xf+k\delta)}/10{,}000$$

where Xf=value of the last von Frey hair used (log units); k=tabular value (from Chaplan et al. (1994)) for the pattern of positive/negative responses; and δ=mean difference between stimuli (log units). Here δ=0.224.

Von Frey thresholds were converted to percent of maximum possible effect (% MPE), according to Chaplan et al. 1994. The following equation was used to compute % MPE:

$$\% \text{ MPE} = \frac{\text{Drug treated threshold } (g) - \text{allodynia threshold } (g)}{\text{Control threshold } (g) - \text{allodynia threshold } (g)} \times 100$$

ADMINISTRATION OF TEST SUBSTANCE

Rats were injected (subcutaneously, intraperitoneally, intravenously or orally) with a test substance prior to von Frey testing, the time between administration of test compound and the von Frey test varied depending upon the nature of the test compound.

WRITHING TEST

Acetic acid will bring abdominal contractions when administered intraperitoneally in mice. These will then extend their body in a typical pattern. When analgesic drugs are administered, this described movement is less frequently observed and the drug selected as a potential good candidate.

A complete and typical Writhing reflex is considered only when the following elements are present: the animal is not in movement; the lower back is slightly depressed; the plantar aspect of both paws is observable.

(i) Solutions Preparation

Acetic Acid (AcOH):

120 μL of Acetic Acid is added to 19.88 ml of distilled water in order to obtain a final volume of 20 ml with a final concentration of 0.6% AcOH. The solution is then mixed (vortex) and ready for injection.

Compound (Drug):

Each compound is prepared and dissolved in the most suitable vehicle according to standard procedures.

(ii) Solutions Administration

The compound (drug) is administered orally, intraperitoneally (i.p.), subcutaneously (s.c.) or intravenously (i.v.)) at 10 ml/kg (considering the average mice body weight) 20, 30 or 40 minutes (according to the class of compound and its characteristics) prior to testing. When the compound is delivered centrally: Intraventricularly (i.c.v.) or intrathecally (i.t.) a volume of 5 μL is administered.

The AcOH is administered intraperitoneally (i.p.) in two sites at 10 ml/kg (considering the average mice body weight) immediately prior to testing.

(iii) Testing

The animal (mouse) is observed for a period of 20 minutes and the number of occasions (Writhing reflex) noted and compiled at the end of the experiment. Mice are kept in individual "shoe box" cages with contact bedding. A total of 4 mice are usually observed at the same time: one control and three doses of drug.

What is claimed is:

1. A compound of the formula I

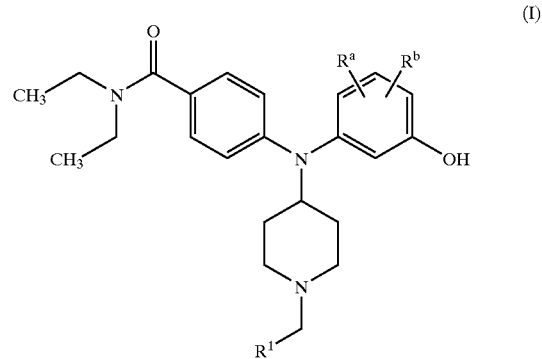

(I)

wherein $R^1$ is selected from any one of (i) phenyl;

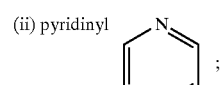

(ii) pyridinyl

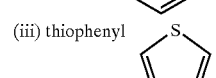

(iii) thiophenyl

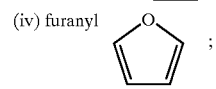

(iv) furanyl

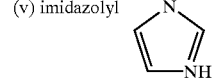

(v) imidazolyl (vi) triazolyl 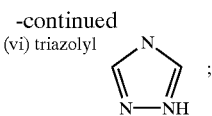

wherein each R¹ phenyl ring and R¹ heteroaromatic ring may optionally and independently be substituted by 1, 2 or 3 substituents selected from the group consisting of: straight and branched $C_1$–$C_6$ alkyl, $NO_2$, $CF_3$, $C_1$–$C_6$ alkoxy, chloro, fluoro, bromo, and iodo, and wherein substitutions on said phenyl ring and on said heteroaromatic ring may take place in any ring position;

$R^a$ and $R^b$ is each and independently selected from any one of hydrogen, a straight and branched $C_1$–$C_6$ alkyl, $NO_2$, $CF_3$, $C_1$–$C_6$ alkoxy, chloro, fluoro, bromo, and iodo;

as well as pharmaceutically acceptable salts thereof.

2. A compound according to claim 1, wherein $R^a$ and $R^b$ are both hydrogen.

3. A compound according to claim 1 or 2, wherein said 1, 2 or 3 substituents are selected from the group consisting of: a straight or branched $C_1$–$C_6$ alkyl, $NO_2$, $CF_3$, $C_1$–$C_6$ alkoxy, chloro, fluoro, bromo, and iodo.

4. A compound, selected from;

N,N-diethyl-4-[[(3-hydoxyphenyl)[1-(phenylmethyl)-4-piperidinyl]-amino]benzamide;

N,N-diethyl-4-[(2-bromo-5-hydroxyphenyl)[1-(phenylmethyl)-4-piperidinyl]-amino]benzamide;

N,N-diethyl-4-[(5-hydroxy-2-iodophenyl)[1-(phenylmethyl)-4-piperidinyl]-amino]benzamide;

4-[(2-chloro-5-hydroxyphenyl)[1-(phenylmethyl)-4-piperidinyl]amino]-N,N-diethyl-benzamide;

N,N-diethyl-4-[(2-fluoro-5-hydroxyphenyl)[1-(phenylmethyl)-4-piperidinyl]-amino]benzamide;

N,N-diethyl-4-[[1-(3-furanylmethyl)-4-piperidinyl](3-hydroxyphenyl)-amino]benzamide;

N,N-diethyl-4-[(3-hydroxyphenyl)[1-(3-thienylmethyl)-4-piperidinyl]-amino]benzamide;

N,N-diethyl-4-[(3-hydroxyphenyl)[1-[[4-(trifluoromethyl)phenyl]methyl]-4-piperidinyl]-amino]benzamide;

N,N-diethyl-4-[(3-hydroxyphenyl)[1-[(4-iodophenyl)methyl]-4-piperidinyl]-amino]benzamide;

N,N-diethyl-4-[[1-[(4-bromophenyl)methyl]-4-piperidinyl](3-hydroxyphenyl)-amino]benzamide;

N,N-diethyl-4-[[1-[(4-chlorophenyl)methyl]-4-piperidinyl](3-hydroxyphenyl)-amino]benzamide;

N,N-diethyl-4-[[1-[(4-fluorophenyl)methyl]4-piperidinyl](3-hydroxyphenyl)-amino]benzamide;

4-[[1-[(2,4-dichlorophenyl)methyl]-4-piperidinyl](3-hydroxyphenyl)amino]-N,N-diethyl-benzamide;

N,N-diethyl-4-[[1-[(3-fluorophenyl)methyl]4-piperidinyl](3-hydroxyphenyl)-amino]benzamide;

N,N-diethyl-4-[[1-[(2-fluorophenyl)methyl]-4-piperidinyl](3-hydroxyphenyl)-amino]benzamide; and N,N-diethyl-4-[(3-hydroxyphenyl)[1-[(4-methylphenyl)methyl]-4-piperidinyl]-amino]benzamide.

5. A compound according to any of the preceding claims, in the form of its hydrochloride, sulfate, tartrate or citrate salt.

6. A pharmaceutical composition comprising a therapeutically effective amount of a compound according to claim 1 as an active ingredient, together with a pharmacologically and pharmaceutically acceptable carrier.

7. A method for treating a subject for pain, comprising administering an effective amount of a compound according to claim 1 is to said subject.

8. A method for treating a subject for a gastrointestinal disorder, comprising administering an effective amount of a compound according to claim 1 to said subject.

9. A method for treating a subject for a spinal injury comprising administering an effective amount of a compound according to claim 1 to said subject.

10. A compound of the formula II

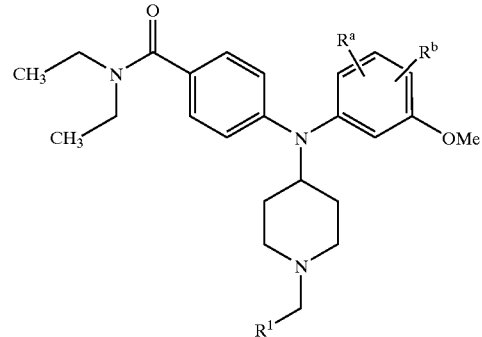

wherein
R¹ is selected from any one of (ii) pyridinyl 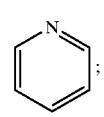

(iii) thiophenyl 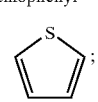

(iv) furanyl 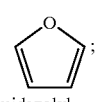

(v) imidazolyl 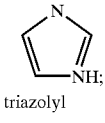

(vi) triazolyl 

wherein each R¹ phenyl ring and R¹ heteroaromatic ring may optionally and independently be substituted by 1, 2 or 3 substituents selected from the group consisting of: a straight and branched $C_{1-6}$ alkyl, $NO_2$, $CF_3$, $C_{1-6}$ alkoxy, chloro, fluoro, bromo, and iodo and wherein substitutions on said phenyl ring and on said heteroaromatic ring may take place in any ring position and wherein $R^a$ and $R^b$ is each and independently selected from any one of hydrogen, a straight and branched $C_1$–$C_6$ alkyl, $NO_2$, $CF_3$, $C_{1-6}$ alkoxy, chloro, fluoro, bromo, and iodo; and with the proviso that when R¹ is phenyl, $R^a$ and $R^b$ are not both hydrogen.

* * * * *